US012584103B2

(12) United States Patent
Miller et al.

(10) Patent No.: US 12,584,103 B2
(45) Date of Patent: Mar. 24, 2026

(54) HYPOTHERMIC 3D BIOPRINTING OF LIVING TISSUES SUPPORTED BY PERFUSABLE VASCULATURE

(71) Applicant: WILLIAM MARSH RICE UNIVERSITY, Houston, TX (US)

(72) Inventors: Jordan Miller, Houston, TX (US); Anderson Ta, Houston, TX (US); Bagrat Grigoryan, Spring, TX (US)

(73) Assignee: WILLIAM MARSH RICE UNIVERSITY, Houston, TX (US)

( * ) Notice: Subject to any disclaimer, the term of this patent is extended or adjusted under 35 U.S.C. 154(b) by 0 days.

(21) Appl. No.: 18/654,976

(22) Filed: May 3, 2024

(65) Prior Publication Data

US 2024/0352408 A1 Oct. 24, 2024

Related U.S. Application Data

(60) Continuation of application No. 17/849,904, filed on Jun. 27, 2022, now Pat. No. 11,976,294, which is a continuation of application No. 17/071,923, filed on Oct. 15, 2020, now Pat. No. 11,371,014, which is a division of application No. 15/709,392, filed on Sep. 19, 2017, now Pat. No. 10,844,350, which is a continuation of application No. PCT/US2016/023302, filed on Mar. 18, 2016.

(60) Provisional application No. 62/136,004, filed on Mar. 20, 2015.

(51) Int. Cl.
| | |
|---|---|
| *C08F 2/46* | (2006.01) |
| *B29C 64/129* | (2017.01) |
| *B29C 64/393* | (2017.01) |
| *B33Y 10/00* | (2015.01) |
| *B33Y 50/02* | (2015.01) |
| *B33Y 70/00* | (2020.01) |
| *C08F 2/50* | (2006.01) |
| *C08G 61/04* | (2006.01) |
| *C12M 1/12* | (2006.01) |
| *C12M 3/00* | (2006.01) |
| *C12N 5/00* | (2006.01) |
| *C12N 5/078* | (2010.01) |
| *B29K 71/00* | (2006.01) |

(52) U.S. Cl.
CPC .......... *C12N 5/0062* (2013.01); *B29C 64/129* (2017.08); *B29C 64/393* (2017.08); *B33Y 10/00* (2014.12); *B33Y 50/02* (2014.12); *B33Y 70/00* (2014.12); *C12M 3/00* (2013.01); *C12M 21/08* (2013.01); *C12M 25/14* (2013.01); *C12N 5/0068* (2013.01); *C12N 5/0641* (2013.01); *B29K 2071/02* (2013.01); *C12N 2513/00* (2013.01); *C12N 2533/30* (2013.01); *C12N 2537/00* (2013.01)

(58) Field of Classification Search
CPC ......... B33Y 10/00; B33Y 70/00; B33Y 50/02; C12N 5/0641; C12N 5/0068; C12N 5/0062; C12N 2537/00; C12N 2533/30; C12N 2513/00; C12M 3/00; C12M 25/14; C12M 21/08; B29C 64/129; B29C 64/393; B29K 2071/02
USPC .................. 264/401; 522/71, 189, 184, 1, 6
See application file for complete search history.

(56) References Cited

U.S. PATENT DOCUMENTS

| | | | |
|---|---|---|---|
| 8,507,569 B2 | 8/2013 | Kura et al. | |
| 2004/0202625 A1 | 10/2004 | Daniloff et al. | |
| 2006/0022379 A1 | 2/2006 | Wicker et al. | |
| 2006/0237880 A1 | 10/2006 | Wicker et al. | |
| 2008/0102122 A1 | 5/2008 | Mahadevan et al. | |
| 2009/0042170 A1 | 2/2009 | Chen et al. | |
| 2009/0130756 A1* | 5/2009 | Klann | A01N 1/10 435/395 |
| 2010/0055484 A1 | 3/2010 | Chretien et al. | |
| 2010/0127433 A1 | 5/2010 | Medina et al. | |
| 2010/0303804 A1 | 12/2010 | Liska et al. | |
| 2012/0058174 A1 | 3/2012 | West et al. | |
| 2012/0165491 A1 | 6/2012 | Ootsuki et al. | |
| 2013/0095049 A1 | 4/2013 | Feo et al. | |
| 2013/0107201 A1 | 5/2013 | Argal et al. | |
| 2013/0243878 A1 | 9/2013 | Mariner et al. | |
| 2013/0295212 A1 | 11/2013 | Chen et al. | |
| 2013/0345794 A1 | 12/2013 | Khatiwala et al. | |
| 2015/0057786 A1 | 2/2015 | Murphy et al. | |

FOREIGN PATENT DOCUMENTS

| | | | | |
|---|---|---|---|---|
| WO | 2014189835 | 11/2014 | | |
| WO | WO-2016154070 A1 * | 9/2016 | .......... | B29C 64/129 |

OTHER PUBLICATIONS

International Search Report and Written Opinion, dated Aug. 11, 2016, in corresponding International Patent Application No. PCT/US16/23302.
Fairbanks B.D. et al. "Photoinitiated polymerization of PEG-diacrylate with lithium phenyl-2,4,6 trimethylbenzoylphosphinate: polymerization rate and cytocompatibility", Biomaterials [online], Sep. 23, 2009 (Sep. 23, 2009) [Retrieved on May 16, 2016], vol. 30, Issue 35, retrieved from the Internet: <DOI: 10.1016/jbiomaterials. 2009.08.055>, pp. 6702-6707.

(Continued)

*Primary Examiner* — Jessica Whiteley
(74) *Attorney, Agent, or Firm* — Reed Smith LLP; Hallie H. Wimberly; Richard J. Brown

(57) ABSTRACT

The present disclosure provides compositions and methods for producing hydrogel matrix constructs. Methods of using hydrogel matrix constructs for tissue repair and regeneration and for the oxygenation of red blood cells are also disclosed.

7 Claims, 36 Drawing Sheets

(56)                References Cited

OTHER PUBLICATIONS

Atala A. et al. "Tissue-engineered autologous bladders for patients needing cystoplasty." Lancet. Apr. 15, 2006; 367 (9518):1241-6.

Gauvin R. et al. "Microfabrication of complex porous tissue engineering scaffolds using 3D projection stereolithography." Biomaterials. 2012; 33: 3824-3834.

Heimbach D. et al. "Artificial dermis for major burns. A multi-center randomized clinical trial." Ann Surg. Sep. 1988; 208(3):313-20.

Johnson PC et al. "Strategic directions in tissue engineering." Tissue Eng. Dec. 2007; 13(12):2827-37.

Jun HW et al. "Endothelialization of Microporous YIGSR/PEG-Modified Polyurethaneurea." Tissue Eng. Jul.-Aug. 2005; 11(7-8):1133-40.

Khademhosseini A et al. "Microengineered hydrogels for tissue engineering." Biomaterials. Dec. 2007; 28 (34):5087-92.

Ko HC et al. . "Engineering thick tissues—the vascularisation problem." Eur Cell Mater. 2007; 14:1-18; discussion 18-9.

Kolesky DB "3D Bioprinting of Vascularized, Heterogenous Cell-Laden Tissue Constructs." Advanced Materials. 2014; 26(19); 3124-30.

Nichol JW et al "Cell-laden microengineered gelatin methacrylate hydrogels" Biomaterials. 2010; 31:5536-44.

Lin H et al. Application of visible light-based projection stereolithography for live cell-scaffold fabrication with designed architecture. Biomaterials. 2013; 34; 331-339.

Nishida K et al. "Corneal reconstruction with tissue-engineered cell sheets composed of autologous oral mucosal epithelium." N Engl J Med. Sep. 16, 2004; 351(12):1187-96.

Ciocci et al., "Scaffold-in-Scaffold Potential to Induce Growth and Differentiation of Cardiac Progenitor Cells", Stem Cells and Development, v 26, p. 1438-1447, Oct. 1, 2017.

Harley BA., Lynn AK., Wissner-Gross Z., Bonfield W., Yannas IV. Gibson LJ. "Design of a multiphase osteochondral scaffold III: Fabrication of layered scaffolds with continuous interfaces". J Biomed Mater Res A. 2010; 3:1078-93. PMID: 19301263.

Yannas IV, Burke JF, Orgill DP, Skrabut EM. "Wound tissue can utilize a polymeric template to synthesize a functional extension of skin." Science. Jan. 8, 1982; 215(4529):174-6. PMID: 7031899.

* cited by examiner

Fig. 3B 6 kDa 15 wt.% PEGDA
0 – 0.18 wt% Tartrazine 100 um Gap

T = 2 min                T = 15 min

Ladder Rendering        IVIS Perfusion Experiments t = 0 min                t = 20 min

HYPOTHERMIC 3D BIOPRINTING OF LIVING TISSUES SUPPORTED BY PERFUSABLE VASCULATURE

CROSS-REFERENCE TO RELATED APPLICATIONS

The present application is a continuation application of U.S. application Ser. No. 17/849,904, filed Jun. 27, 2022; which is a continuation application of U.S. application Ser. No. 17/071,923, filed Oct. 15, 2020, now U.S. Pat. No. 11,371,014, issued Jun. 28, 2022; which is a divisional application of U.S. application Ser. No. 15/709,392, filed Sep. 19, 2017, now U.S. Pat. No. 10,844,350, issued Nov. 24, 2020; which is a continuation application of International Application No. PCT/US16/23302, filed Mar. 18, 2016, which claims priority to U.S. Provisional Application No. 62/136,004, filed on Mar. 20, 2015, the contents of which are incorporated herein by reference.

BACKGROUND

The field of tissue engineering aims to fulfill the great clinical need for development of technologies and processes to facilitate regeneration of human disease or injury by incorporating a combination of cells, biomaterials, and biochemical and physicochemical factors. Indeed, tremendous strides have been achieved over the past several decades to construct implantable avascularized constructs such as skin, cornea, and bladder. However, obtaining functional, physiologically relevant tissues is still a major challenge in the field due to the necessity of a vasculature system to supply nutrients and remove waste in thick constructs. This challenge can be attributed to diffusion transport limitations which results in necrotic cells due to inadequate access to nutrients. Additionally, lack of the ability to recreate the heterogeneous patterns of cells and matrix to obtain constructs with controlled shape and architectures has hindered progress towards organ replacement.

Several approaches have been investigated to facilitate transport of nutrients into engineered tissues. One of the most common approaches utilizes various material processing steps such as critical point drying, gas foaming and salt leaching, or electrospinning to create macroporous structures that can be perfused in vitro for tissue culture. While these processes have yielded templates for the construction of functional tissue with matched mechanical compliance of native tissue and high surface area for delivery of nutrients and oxygen, the precise spatial control of scaffold architecture is not easily achieved with these methodologies given that these constructs contain open, porous void volumes rather than a vessel network.

Additionally, most of the processing steps involved during the fabrication of these engineered tissues require reagents or conditions that are cytotoxic, further limiting their use with the presence of living cells.

Additionally, needle-based molding techniques have been utilized to obtain straight, perfusable channels with natural and synthetic materials. However, advanced constructs that closely resemble the heterogeneity and complexity of tissues cannot be obtained with this technique due to use of a straight needle.

Another approach utilizes soft lithography, a suite of techniques adapted from the microprocessor industry, which offers spatial control of scaffold architecture through photopatterning with photolithography to obtain microfluidic networks. However, these techniques require expensive, proprietary equipment to reach micrometer-scale resolution and this mode of fabrication is much too slow to make large models of organ vasculature efficiently. Additionally, lithography is typically done in Cartesian coordinates to yield channels with rectangular cross-sections. However, native vasculature rarely follows straight x-, y-, or z-vectors, and blood vessels have circular cross-sections. Strategies combining photolithographic processes with layer-by-layer lamination methods have been pursued to achieve multilayered engineered tissues. Unfortunately, the harsh fabrication process and the difficulties in aligning successive layers with high precision and presence of edge-to-edge artifacts limit use of this approach to obtain complex, three-dimensional (3D) interconnected microfluidic networks.

To circumvent challenges associated with manual alignment of layers, multilayered 3D structures have been either manually or automatically fabricated in a layer-by-layer fashion using either 3D projection stercolithography, resulting in the fabrication of an entire layer under a single light exposure (Lin et al. 2013), or deposition techniques, resulting in fabrication of heterogeneous 3D tissue constructs (Kolesky et al. 2014). While these efforts have yielded engineered tissues with spatially patterned cells (Gauvin et al. 2012), they do not resemble complex, physiologically relevant vasculature. Additionally, only hydrogels with a few number of layers have been fabricated thus far.

Although living vascular systems consist of fluidic networks that span from a few centimeters, such as the aorta, to several microns, such as capillaries, the currently available technologies cannot fully capture the whole range of the transport network that is critical for multicellular life. Additionally, most of the current in vitro models contain 3D constructs with a single vascular network containing one inlet and one outlet. However, a key feature of complex biological systems, the presence of interpenetrating vascular networks, is lacking in current literature but central to mammalian physiology for sufficient transport of nutrients. For example, the alveolus must be located in close proximity to the pulmonary capillary network to ensure oxygenation of red blood cells due to the passive transport nature of oxygen.

SUMMARY

To bypass the limitations of the methods described above, the present disclosure relates to improved polymer compositions, such as a prepolymerization solution, for use with 3D printers that utilize digital light processing (DLP) to fabricate thick, physiologically relevant vascular networks with and without cells. The designed 3D printer is an automated, computer-aided 3D prototyping device which utilizes additive manufacturing to selectively pattern photosensitive biomaterials one layer at a time, yielding a 3D tissue engineered construct. The printer contains a mobile Z-axis stage that is lowered toward the build platform which contains a vat with the prepolymerization solution containing photosensitive polymers and a photoinitiator. Exposure of a pattern from a commercially available digital light projection device is displayed on the inner bottom surface of the vat, resulting in a specific 3D patterned hydrogel layer. After the material undergoes gelation, the Z-axis stage automatically moves up to the next layer height and the process is automatically repeated until the final construct is obtained. Additionally, a syringe setup implemented with the 3D bioprinter can automatically dispense more prepolymerization solution during the printing process, as necessary. The printer is also designed so that multiple materials can be automatically printed with this technique. Photopolymerizable biomaterials that can be used with this printer include, but are not limited to, acrylates, acrylamides, and methacrylates with molecular weights ranging from 2 to 500 kDa. Photoinitiators that can be used with this printer include those that can absorb in ultraviolet (UV) and/or visible light regions. The novel prepolymerization solutions in this 3D bioprinting method results in the fabrication of a hydrogel matrix with multiple perfusable, tubular channels that have complex architecture that closely resemble and function as native vascular networks.

In some embodiments, the prepolymerization solution comprises a polymer having a molecular weight of greater than 2,000 Daltons and at least two vinyl groups per molecule of polymer, a photoinitiator, and a biocompatible, light-absorbing additive material suitable to control light penetration. In certain embodiments, the prepolymerization solution comprises poly(ethylene glycol) having a molecular weight of greater than 2,000 Daltons and at least two acrylate groups or acrylamide groups per molecule of poly(ethylene glycol), a photoinitiator, a cell, and a biocompatible, light-absorbing additive material suitable to control light penetration.

In certain other embodiments, a composition is provided which includes a hydrogel matrix comprising a plurality of layers, each layer comprising a cross-linked polymer network formed from a photosensitive polymer having a molecular weight greater than 2,000 Daltons, wherein the hydrogel matrix has an elastic modulus of from about 1 kilopascal to about 200 kilopascals. The composition also comprises a first elongated void in the hydrogel matrix providing a first tubular channel and a second elongated void in the hydrogel matrix providing a second tubular channel, wherein the first tubular channel and second tubular channel are perfusable, the first tubular channel does not intersect the second tubular channel, and the second tubular channel interpenetrates the first tubular channel.

In other embodiments, a process for manufacturing a multi-layer hydrogel matrix construct is provided which comprises creating a 3D model of the multi-layer hydrogel matrix construct using a design software, wherein the 3D model of the multi-layer hydrogel matrix construct comprises a first computational algorithm that yields a first elongated void in the multi-layer hydrogel matrix construct providing a first tubular channel, and a second computational algorithm that yields a second elongated void in the multi-layer hydrogel matrix construct providing a second tubular channel wherein the second computational algorithm results in the second tubular channel interpenetrating the first tubular channel. Following the creation of the 3D model, the 3D model is converted to a format suitable for use in a 3D printing software to yield a formatted 3D model which can then be imported into a printing software, wherein the software is programmed to slice the formatted 3D model into multiple two-dimensional (2D) xy images. A prepolymerization solution is then supplied to a vat associated with a build platform of a 3D printer, wherein the vat is transparent, and wherein the prepolymerization solution comprises a photosensitive polymer with a molecular weight of greater than 2,000 Daltons and at least two vinyl groups per molecule of polymer, a light-absorbing additive material to control light penetration, and a photoinitiator. A mobile Z-axis stage of the 3D printer is positioned at a distance from the vat, wherein the Z-axis stage includes a surface sufficient for gelled material to adhere thereto, and wherein the distance between the surface and an inner bottom surface of the vat is equivalent to a desired layer thickness of the multi-layer hydrogel matrix construct. A light source can then be projected through an optical configuration, wherein the projection results in a pattern being displayed on the inner bottom surface of the vat, wherein the pattern corresponds to one of the multiple 2D xy images. After projecting the light source through the optical configuration, the first layer of the multi-layer hydrogel matrix construct can be polymerized by the projected light. The steps of supplying a prepolymerization solution to the vat, positioning the Z-axis stage at a distance from the vat equivalent to a desired layer thickness of the multi-layer hydrogel matrix construct, projection of a light source through an optical configuration to display a pattern on the inner bottom surface of the vat, and polymerizing a layer of the multi-layer hydrogel matrix construct can be repeated for each subsequent layer of the multi-layer hydrogel matrix construct.

In still other embodiments, a method for oxygenating red blood cells in a hydrogel matrix is provided. The method comprises obtaining the hydrogel matrix, wherein the hydrogel matrix comprises a plurality of layers, each layer comprising a cross-linked polymer network formed from a photosensitive polymer having a molecular weight greater than 2,000 Daltons, wherein the hydrogel matrix has a elastic modulus of from about 1 kilopascal to about 200 kilopascals. The hydrogel matrix also comprises a first elongated void in the hydrogel matrix proving a first tubular channel having a first tubular inlet and first tubular outlet, wherein the first tubular inlet and the first tubular outlet are in communication with a fluid supply input line and a fluid supply output line, respectively, wherein the fluid supply input line supplies a fluid to the first tubular channel, and wherein the fluid contains red blood cells. The hydrogel matrix also comprises a second elongated void in the hydrogel matrix providing a second tubular channel having a second tubular inlet and second tubular outlet, wherein the second tubular inlet and the second tubular outlet are in communication with an oxygen supply input line and an oxygen supply output line, respectively, wherein the oxygen supply input line provides oxygen to the second tubular channel, wherein the first tubular channel and the second tubular channel are perfusable, the first tubular channel does not intersect the second tubular channel, and the second tubular channel interpenetrates the first tubular channel. The method further comprises supplying the fluid to the first tubular channel, supplying oxygen to the second tubular channel, and allowing the oxygen from the second tubular channel to oxygenate the red blood cells in the first tubular channel.

The features and advantages of the present invention will be readily apparent to those skilled in the art. While the present disclosure is susceptible to various modifications and alternative forms, specific example embodiments have been shown in the figures and are described in more detail below. It should be understood, however, that the description of specific example embodiments is not intended to limit the invention to the particular forms disclosed, but on the contrary, this disclosure is to cover all modifications and equivalents as illustrated, in part, by the appended claims. Aspects of different embodiments may be combined, as applicable, within the spirit of this disclosure.

BRIEF DESCRIPTION OF DRAWINGS

Some specific example embodiments of the disclosure may be understood by referring, in part, to the following description and the accompanying drawings.

FIG. 3B depicts a photorheological plot demonstrating the kinetics of PEGDA hydrogel as it undergoes gelation with varying concentrations of tartrazine at 100 μm gap size between the parallel plates of the rheometer.

DESCRIPTION

To address the lack of complex vascular models that mimic normal and injured vessel network geometry, the present disclosure further provides a polymer composition, for example a prepolymerization solution comprising an additive that controls light penetration, for use in a 3D printing process that can fabricate 3D engineered tissues with biologically-inspired design criteria including, but not limited to, conforming to Murray's Law, multiscale branched vessels from tens to hundreds of micrometers in diameter, smooth inner walls, circular cross sections, and multiple inlet/outlets. Indeed, with printing parameter optimization, the limit to what can be fabricated depends on what one can model. In addition, more complex designs that contain heterogenous properties in a single layer or in multiple layers can be fabricated with our approach. For instance, grayscale photomasks with predefined gradients can be incorporated to obtain a layer with varied stiffness or for controlled immobilization of biomolecules and cells while still using the same vat and solution. Additionally, utilization of fractal space-filling models to computationally grow vascular networks around and through pre-existing vascular networks or following the architecture of native tissues can be achieved by computer growth models for even more complex and physiologically relevant 3D models. These mathematical fractal, space-filling models can be derived from, for example, knot theory, the Hilbert curve, and the L-system. Such mathematical fractal space-filling models to predict idealized vascular networks include, but are not limited to knot theory, Plumber's Nightmare, Peano curve, Hilbert curve, Pythagoras tree, and Brownian tree models. As an example, the Plumber's Nightmare model essentially comprises two Vascular Ladder models that are connected to each other by straight vertical cylinders. Multiple Plumber's Nightmare models can be intercalated such that they are interpenetrating. The Vascular Ladder models are comprised of 1 inlet and 1 outlet with two horizontal cylinders that are connected by diagonal cylinders, resulting in interchannel junctions.

Figure 3A:
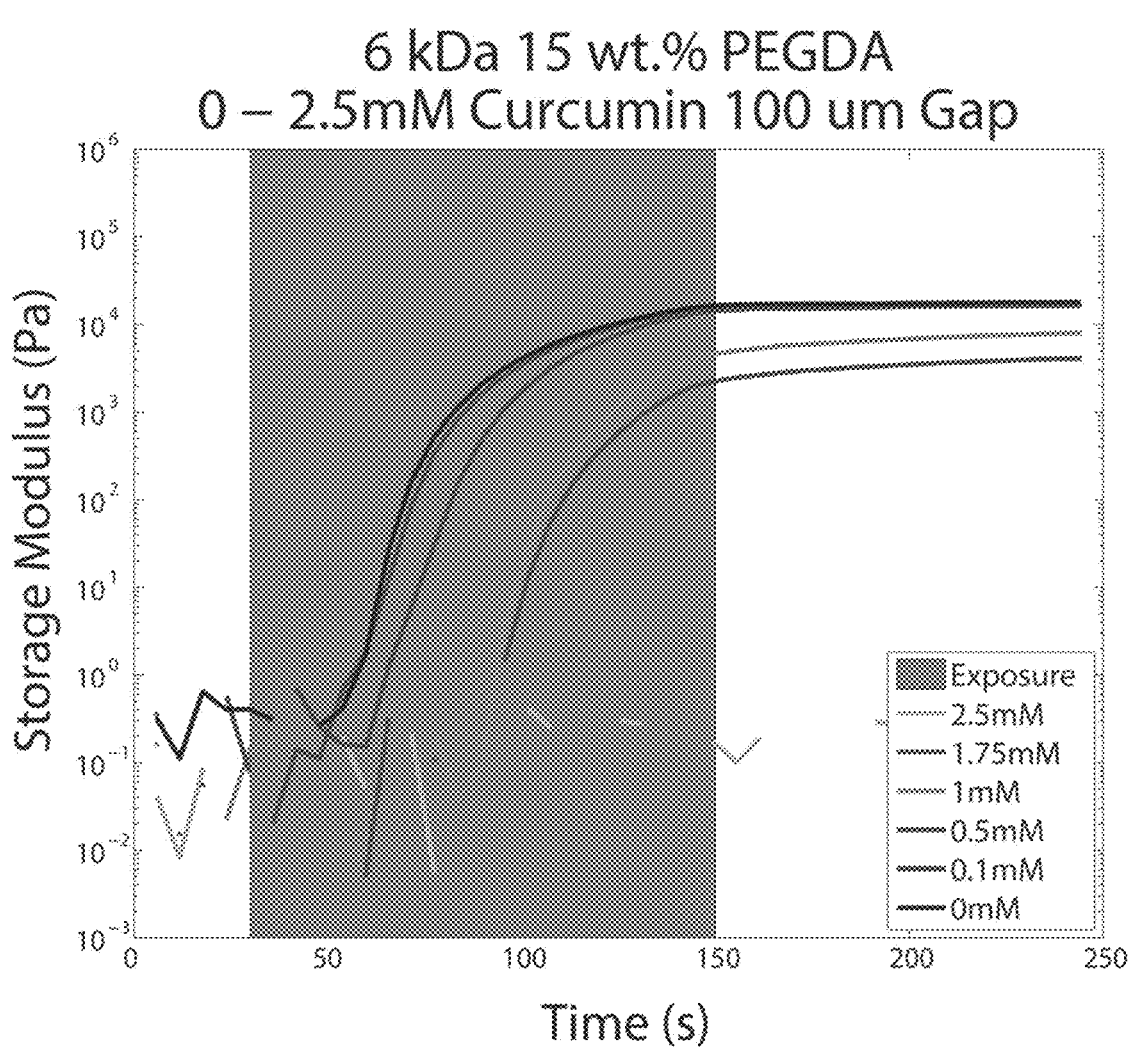
FIG. 3A depicts a photorheological plot demonstrating the kinetics of PEGDA hydrogel as it undergoes gelation with varying concentrations of curcumin at 100 μm gap size between the parallel plates of the rheometer.
Figure 3B:
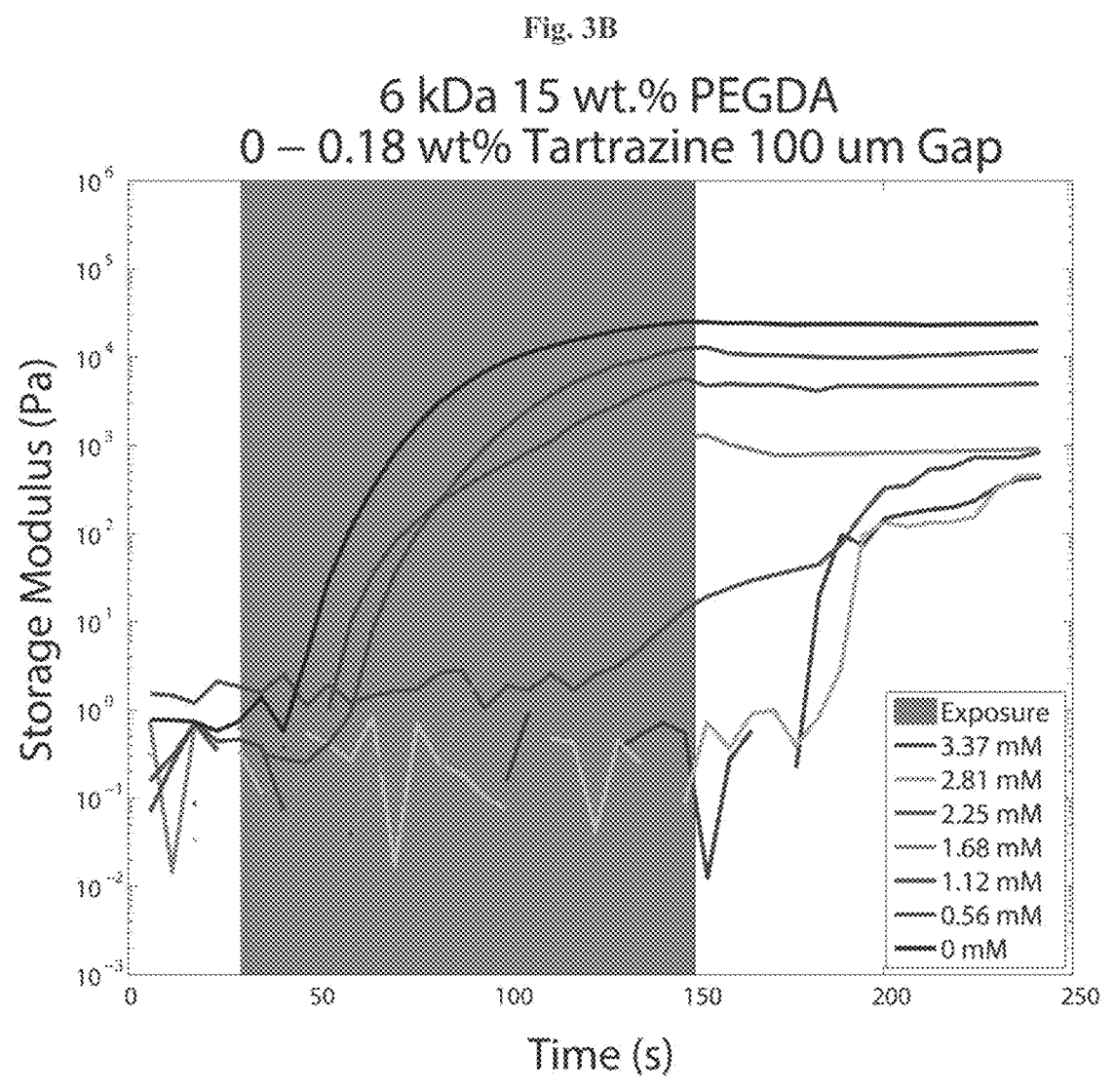

Photopolymerizable hydrogel materials such as poly(ethylene glycol) diacrylate (PEGDA) can be crosslinked using a photoinitiator system such as lithium acylphosphinate (LAP) (Fairbanks et al. 2009) which absorbs in the UV to visible light wavelength range. By adding, for example, low concentrations of carbon black (which can absorb light across all UV-visible light spectrum), or low concentrations of tartrazine (which has a peak light absorption near 500 nm) we can limit the depth of penetration of light. To quantify this process we developed a photorheology assay to monitor hydrogels polymerization and stiffness evolution as a function of light dosage and sample thickness (sec FIGS. 3A-3B). Indeed, the addition of additive materials, such as tartrazine, control the extent of gelation of the prepolymerization mixture by impacting the gelation kinetics and final gel rheological properties.

To achieve complex patterning of multilayered hydrogels, on the order of several centimeters, with high pattern fidelity, light exposure during the printing process is controlled so that the light projected onto the build platform interacts mainly with the layer that undergoes gelation for either partial or complete gelation. Radical mediated photopolymerization of hydrogels utilizes a photoinitiator—a molecule sensitive to a particular wavelength range that, upon light absorption, the molecule decays and release free radicals which can catalyze hydrogel polymerization. To this end, it is imperative to quantify the wavelength sensitivity of the photoinitiator. High concentrations of photoinitiator will absorb more light and could provide higher z-resolution by limiting penetration depth of the incident light. However, high photoinitiator concentrations disrupt the photopolymerization reaction (more free radicals have a higher chance of annihilating each other), and photoinitiators at high concentrations are cytotoxic. In addition, with high x-y resolution from the projector, a complication is that light shines through the z-direction of the previously printed layers, potentially limiting the ability to form complex overhang structures (such as found in vasculature), and also may cause phototoxicity to entrapped cells.

Figure 1A:
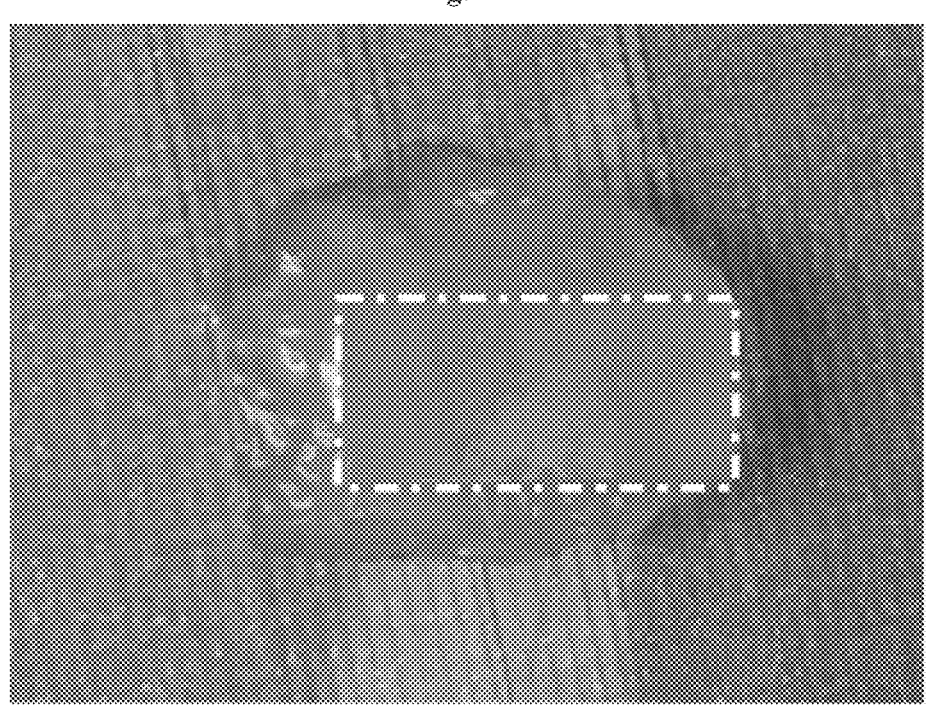
FIG. 1A includes a photograph of a hydrogel printed with red fluorescent beads added to the prepolymerization solution. The area in the dashed white box indicates the actual model printed whereas the gelled material outside of the dashed white border is formed due to overcuring due to light scattering during the printing process.
Figure 1B:
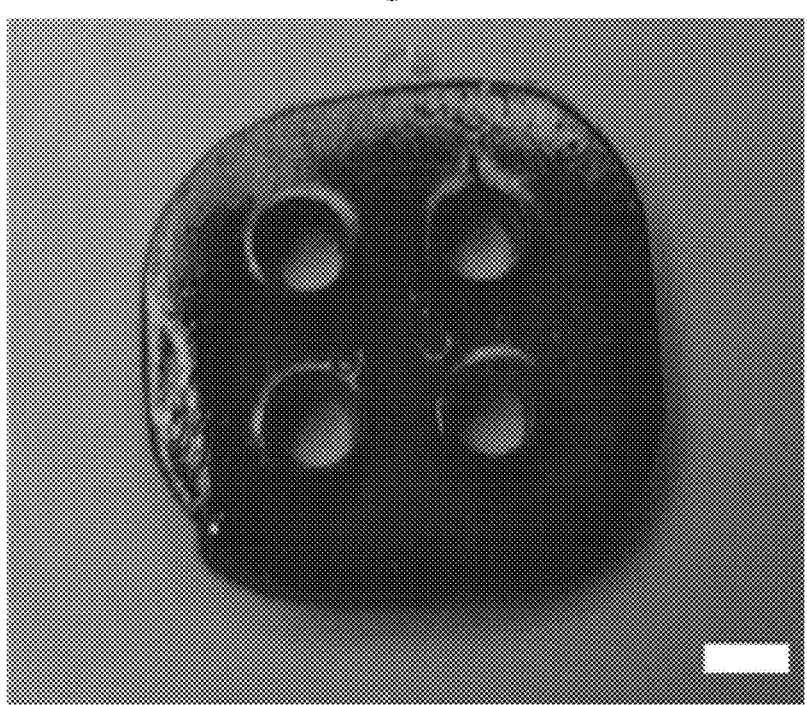
FIG. 1B includes a photograph of a poly(ethylene glycol) diacrylate (PEGDA) hydrogel printed with carbon black as the additive material in the prepolymerization solution. Scale bar=2 mm.
Figure 1C:
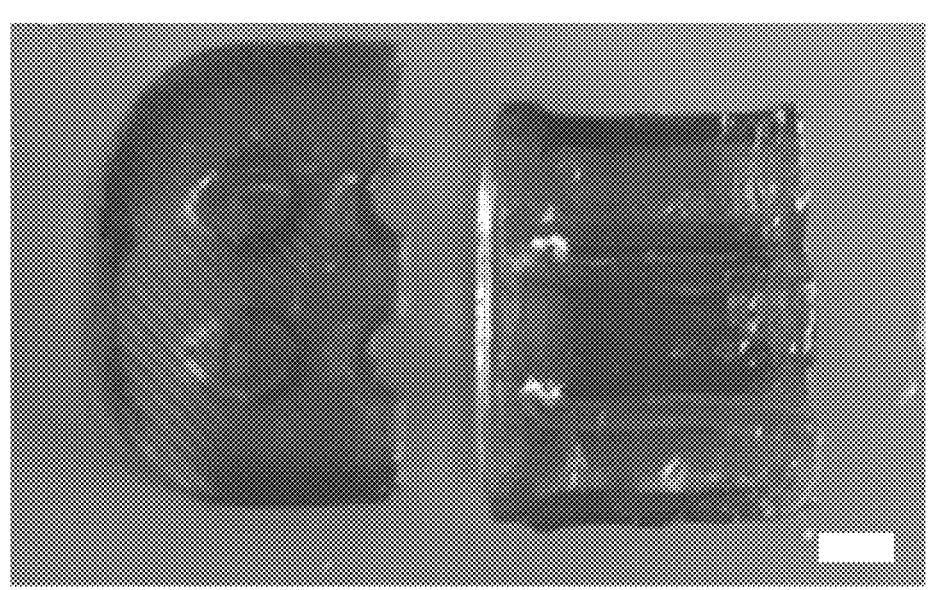
FIG. 1C includes a photograph of a PEGDA hydrogel printed with commercial ink as the additive material in the prepolymerization solution. Scale bar=2 mm.
Figure 1D:
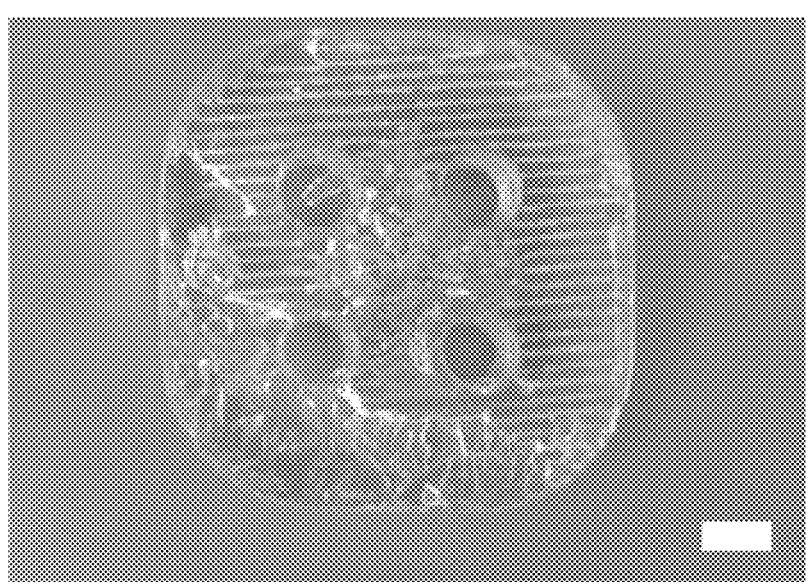
FIG. 1D includes a photograph of a hydrogel printed with yellow food coloring as the additive material in the prepolymerization solution. Scale bar=2 mm.
Figure 2A:
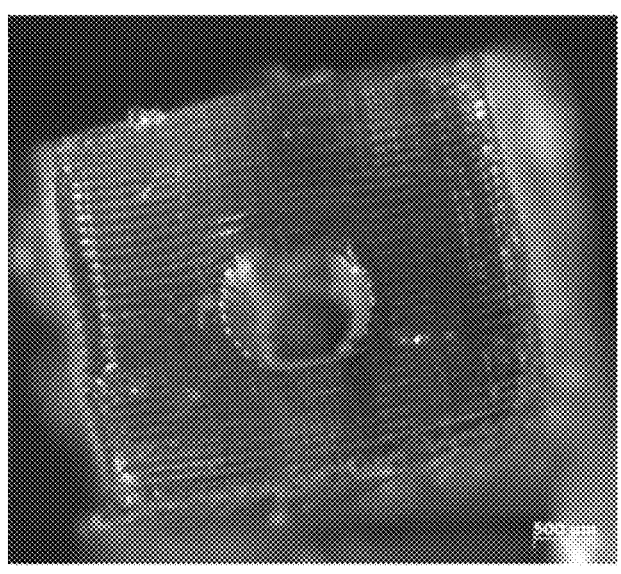
FIG. 2A includes a photograph of the end of a 1 mm channel in a PEGDA hydrogel, showing the open inlet and horizontal layers of printing.
Figure 2B:
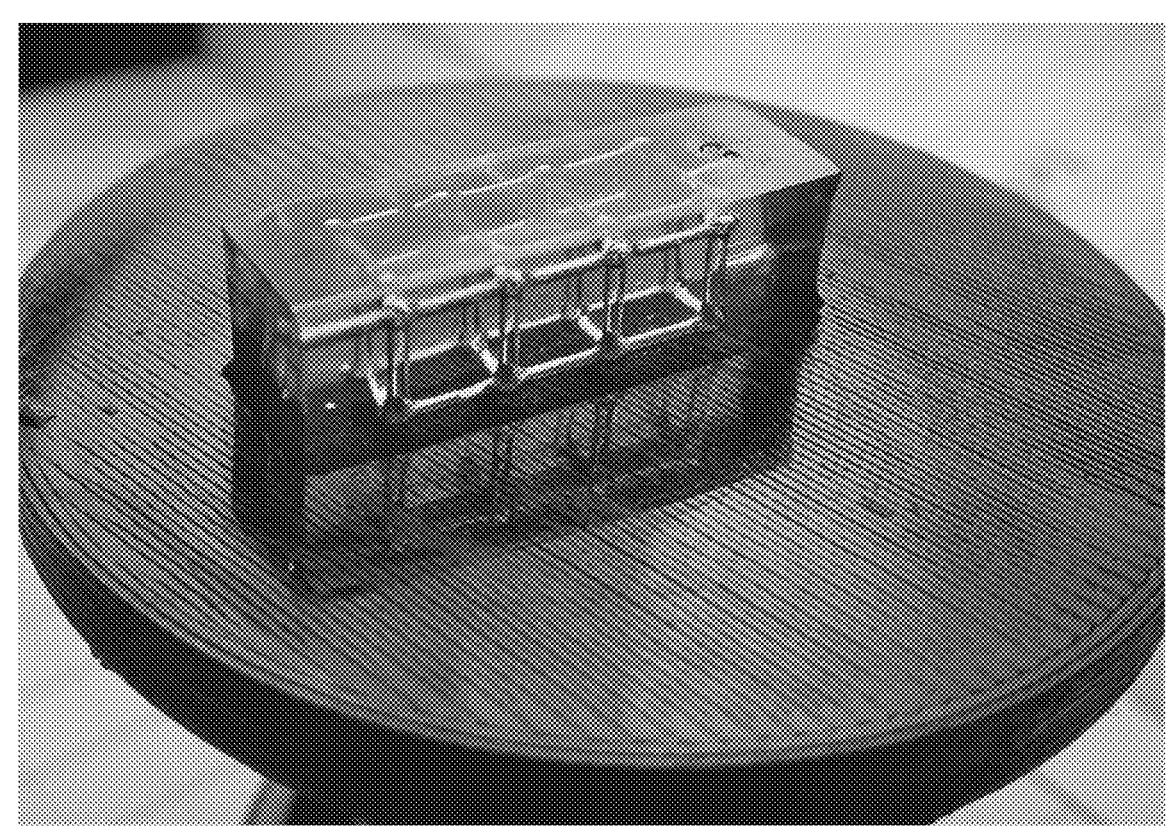
FIG. 2B includes a photograph of a 3D printed PEGDA hydrogel showing the open vascular channel of the Plumber's Nightmare model.

Thus, to achieve high resolution printing, the present disclosure provides a photochemical means to provide, for the first time, high z-resolution in bioprinted tissues while maintaining high cell viability. To address the concerns outlined above we have identified a general strategy whereby biocompatible materials or chemicals are added to the prepolymerization solution to provide higher z-resolution. The additive material is selected based on three criteria: 1) ability to absorb light wavelengths which fully encompass the photosensitive wavelength range of the photoinitiator, 2) limited participation or limited inhibition of photopolymerization reactions, and 3) biocompatibility at the concentrations desired. This additive material is referred to herein as a biocompatible, light-absorbing additive material suitable to control light penetration. Multiple molecules have been screened that absorb light, limiting the penetration depth of light into already formed layers (sec FIGS. 1A-1D). As observed in FIG. 1A, significant overcuring, evidenced by the polymerization outside of the white box, is observed when printing with red fluorescent beads added to the prepolymerization solution. However, as shown in FIGS. 1B-1D, the addition of carbon black (FIG. 1B), commercial ink (FIG. 1C), and yellow food coloring (FIG. 1D) limited overcuring, allowing for the printing of higher resolution structures such as tubes and holes. Suitable molecules absorb in the same region as the photoinitiator used in the prepolymerization solution. Examples of molecules capable of controlling light penetration and therefore suitable for use as the biocompatible, light-absorbing additive material include carbon black, yellow food coloring, tartrazine, nanoparticles, microparticles, gold nanoparticles, riboflavin, phenol red, Beta-carotene, curcumin, saffron, and turmeric. Proteins may also act as suitable biocompatible, light-absorbing additive materials provided that their peak absorption overlaps with the peak absorption of the photoinitiator and matched to the incident light source. Additionally, we recognize that cells that are transfected or transduced with proteins that absorb in the same region as the photoinitiator, such as cyan fluorescent protein (CFP) or green fluorescent protein (GFP), can be used at high concentrations, with reduced or no additives, to result in reduced lateral overcuring due to the light absorbing molecules present inside cells. Additionally, our methodology allows us to print hydrogels with both horizontal and vertical channels due to stringent control of the penetration of the projected light (see FIGS. 2A and 2B).

To address potential cell viability concerns associated with long print times for fabrication of engineered tissues with this method, the cell viability can be maintained or enhanced in multiple ways. One method involves lowering the metabolic activity of the cells by printing in hypothermic conditions. Similar to hypothermic preservation of solid organs for extended preservation of transplant organs (typically done at 4° C.), decreasing the temperature in which cells are printed in will significantly decrease cellular metabolism. For example, we have demonstrated that a cold room (4° C.) can be utilized to achieve hypothermic bioprinting. Additionally, incorporation of vitamins, growth factors, or serum in the prepolymerization solution, for readily accessible supply of nutrients, can be done to maintain or enhance cell viability. Importantly, photopolymerization is highly tolerant of decreased temperatures with only a modest increase in required exposure time. Further, decreasing the temperature of the entire 3D printing apparatus and reagents may help to quench heat generated from incident light or the photopolymerization process. In addition, molecules such as PEG and glycerol have been widely used as cryoprotectants in cell culture. Thus, use of a polymer such as PEG during the hypothermic printing process may enhance cell survivability.

Branching multi-scale transport systems are found in all multicellular life. Similar to the highly complex branching structure of vascular networks, the respiratory tree is also composed of a complex branching structure for sufficient supply of air in the distal regions of the lung. It has been indicated that endothelial cells may aid in lung epithelial branching. However, current manufacturing techniques do not allow for structures that mimic the anatomical complexity of native lung tissue. By using 3D printing, it should be possible to produce structures that mimic the anatomical complexity of native lung tissue and vasculature. The proposed approach can allow the printing of such structures and for embedding endothelial and epithelial cell types in channel lumens to mimic vascular and respiratory networks. The circular cross-sections attainable permit the development of confluent cell layers along the channel lumens. Given the higher z-resolution under the proposed approach, the channels can more closely mimic vascular and respiratory networks. The disclosed methods and materials can enable the fine control of the geometry and architecture of multiple networks. By using fractal, space-filling models akin to physiological vascular networks, the technology permits the design and fabrication of relevant 3D constructs with interpenetrating channels.

Additionally, the proposed approach can be combined with other scaffold fabrication techniques, such as porogen leaching or surface coating, to result in physiologically relevant complex constructs with modified internal microarchitecture or surface properties. Additionally, the proposed approach can be used for fabrication of microfluidic devices for organ-on-a-chip or human-on-a-chip applications.

Additionally, the printer can be modified to include specific sensors for ensuring printing of more precise layer thickness.

The present disclosure provides a novel, unique, inexpensive, fast, efficient method to engineer tissues containing complex vasculature of normal or diseased tissue for in vitro models of tissues or organs. Additionally, the present printing process may be directly translatable in vivo for medical applications, as well as for numerous research and development efforts currently being investigated in the scientific community, such as mechanistic studies of organ development, angiogenesis, vascular remodeling, stem cell and vascular niches, and diseased states of each of these categories, such as for in vitro models of cancer malignancy. For tissue engineering and whole organ replacement, the speed and high throughput nature of the present process, in conjunction with use of appropriate biomaterials, allows for the creation of large, physiologically relevant model vasculature on the order of a few hours. Combined with the inexpensive nature of the equipment required, the presently disclosed process lends itself well to mass production of whole organ vasculature.

Prepolymerization Solution

In certain embodiments, a prepolymerization solution is provided. The prepolymerization solution comprises a photosensitive polymer having a molecular weight greater than 2,000 Daltons, a photoinitiator, and a biocompatible, light-absorbing additive material suitable to control light penetration. In some embodiments, the prepolymerization solution can also include one or more living cells (referred to herein simply as a cell). In some aspects, the prepolymerization solution can include a cryoprotectant such as low molecular weight PEG, glycerol, ethylene glycol, sucrose, propylene glycol, trehalose, raffinose, guar gum, xanthan gum, and D-mannitol. Cryoprotectants can be permeating or non-permeating. Each of these components is described in further detail herein. The prepolymerization solution can also include a water content of 10 wt % to about 99.5 wt %. The prepolymerization solution can include a water content of 80 wt % to about 90 wt %. In some aspects, the prepolymerization can further comprise DMEM media, serum, proteins, growth factors, thickening agents and/or anti-clumping components. Such components can provide nutrition for and/or neutral buoyancy for cells in the prepolymerization solution.

Photosensitive Polymer

In certain embodiments, a photosensitive polymer having a molecular weight greater than 2,000 Daltons can be used. Photosensitive polymers can include at least two vinyl groups per molecule of polymer. Such vinyl groups can include acrylate, acrylamide and methacrylate. Photosensitive polymers which can be used include, by example but not limitation, poly(ethylene glycol) diacrylate (PEDGA), cell-adhesive poly(ethylene glycol), MMP-sensitive poly(ethylene glycol), poly(ethylene glycol) dimethacrylate (PEGDMA), poly(ethylene glycol) diacrylamide (PEGDAAm), gelatin methacrylate (GelMA), methacrylated hyaluronic acid (MeHA), and PEGylated fibrinogen. The photosensitive polymers can also be modified by the conjugation of peptides such as CGRGDS.

Photoinitiator

In certain embodiments, a photoinitiator can be used. The photoinitiator is a molecule sensitive to a particular wavelength range that, upon light absorption, the molecule decays and releases free radicals which can catalyze hydrogel polymerization. Such photoinitiators can include, by way of example but not limitation, lithium acylphosphinate, Irgacure 2959, the Eosin Y system (consisting of cosin Y, 1-vinyl-2-pyrrolidinone (NVP), and triethanolamine (TEA)), tris(triphenlphosphine)ruthenium(II), and camphorquinone which is typically used with either ethyl 4-N, N-dimethylaminobenzoate or TEA and the photosensitizer isopropyl thioxanthone. High concentrations of photoinitiators can be used to achieve increased z-resolution by limiting the penetration depth of incident light, however, these high concentrations can disrupt the photopolymerization reaction and are cytotoxic. In addition, because light can shine through previously printed layers, use of high concentrations of photoinitiators can limit the ability to print complex overhang structures and cause phototoxicity to entrapped cells.

Biocompatible, Light-absorbing Additive Material

In certain embodiments a biocompatible, light-absorbing additive material can be used. The biocompatible, light-absorbing additive material is selected based on three criteria: 1) ability to absorb light wavelengths which fully encompass the photosensitive wavelength range of the photoinitiator, 2) limited participation or limited inhibition of photopolymerization reactions, and 3) biocompatibility at the concentrations desired. The biocompatible, light-absorbing additive material can be organic. The biocompatible, light-absorbing additive material can include, by way of example, but not limitation carbon black, yellow food coloring, tartrazine, nanoparticles, microparticles, gold nanoparticles, riboflavin, phenol red, Beta-carotene, curcumin, saffron, and turmeric. Additionally, cells that are transfected or transduced with proteins that absorb in the same region as the photoinitiator, such as cyan fluorescent protein (CFP) or green fluorescent protein (GFP), can be used at high concentrations, with reduced or no additives, to result in reduced lateral overcuring due to the light absorbing molecules present inside cells. The biocompatible, light-absorbing additive material enables printing of hydrogels with both horizontal and vertical channels due to stringent control of the penetration of the projected light which allows for high z-resolution as the penetration of light into already printed layers is reduced.

A Cell

In certain embodiments, a cell may be included in the prepolymerization solution and/or hydrogel. Such cells can include endothelial and epithelial cell types. Such cells can be human mesenchymal stem cells (hMSCs). By way of example but not limitation, epithelial cells can include human bronchial epithelial cells (HBECs), columnar ciliated epithelial cells, mucous cells, serous cells, basal cells, Clara cells, neuroendocrine cells, type I and type II alveolar cells, and A549 adenocarcinoma human alveolar basal epithelial cells. By way of example but not limitation, epithelial cells can be characterized based on staining for E-cadherin, surfactant proteins A, C and D, basal marker keratin 14, and TTF-1 Similarly, by way of example but not limitation, endothelial cells can include human umbilical vein endothelial cells (HUVECs), human pulmonary microvascular endothelial cells, and induced pluripotent endothelial cells. By way of example but not limitation, endothelial cells can be characterized based on statining for platelet endothelial cell adhesion molecular (PECAM/CD31) and vascular endothelial (VE)-cadherin.

Hydrogel Matrix

In some embodiments, a hydrogel matrix is provided. The hydrogel matrix can include a first tubular channel and a second tubular channel. The hydrogel matrix can be porous. The hydrogel matrix can also include a first cell type and a second cell type embedded therein. In certain aspects, the hydrogel matrix can include a first cell type embedded therein.

The hydrogel matrix can be produced in one or more layers and in certain embodiments, will include more than 1,000 layers, from about 10 layers to about 2,000 layers, from about 10 layers to about 1,000 layers, from about 10 to about 500 layers, from about 10 to about 100 layers, from about 100 to about 2,000 layers, from about 100 to about 1,000 layers, from about 100 layers to 500 layers, from about 100 layers to about 300 layers, from about 500 layers to about 1,000 layers, from about 500 layers to about 2,000 layers, from about 1,000 layers to about 2,000 layers, and any range therebetween of the above. In certain embodiments, each layer can have a thickness of from about 25 microns to about 100 microns, from about 50 microns to about 100 microns, from about 25 microns to about 50 microns, and any range therebetween. In certain other aspects, each layer can have a thickness of 50 microns. In still other aspects, each layer can have a thickness of less than 50 microns. In some embodiments, each layer can have a thickness of 25 microns. In certain aspects, each layer can have a thickness of 100 microns. In certain aspects, the one or more layers of the hydrogel matrix can include a first cell type wherein one or more other layers of the hydrogel matrix include a second cell type, but not the first cell type.

The one or more layers of the hydrogel matrix can have cells embedded therein. In certain aspects, the one or more layers of the hydrogel matrix adjacent to the one or more layers of the hydrogel matrix with embedded cells comprises an extracellular matrix protein.

The one or more layers of the hydrogel matrix can be formed from a photosensitive polymer. In certain aspects, the one or more layers of the hydrogel matrix can be formed from a second photosensitive polymer. The one or more layers of the hydrogel matrix can each include a first portion and second portion. In certain aspects, the first portion is formed from the photosensitive polymer and the second portion is formed from a second photosensitive polymer having a molecular weight of greater than 2,000 Daltons. In certain aspects, the first portion can include a first cell type embedded therein and the second portion can include a second cell type embedded therein, wherein the first cell type is different from the second cell type. In certain aspects, the first portion can include a first fluorophore and the second portion can include a second fluorophore, wherein the first fluorophore is different from the second fluorophore.

Tubular Channels

In some embodiments, a hydrogel can include a first tubular channel and a second tubular channel. In certain aspects, the first and second tubular channel each can include a horizontal segment that intersects more than one layer of the bulk hydrogel matrix. The second tubular channel can interpenetrate the first channel where interpenetrating is defined as the spatial relationship between two channels wherein one channel intersects at least once, a plane between two separate portions of the other channel. The tubular channels can also be branched. For example, the tubular channels may branch, as observed in the torus knot model, wherein the tubular channels reconverge at another point within the hydrogel. However, branched structures can also include channels which extend from the first tubular channel and/or the second tubular channel and terminate within the hydrogel. For, example, tree-like structures can be designed and produced using the present approach. In certain embodiments, the tubular channels have a diameter of 300 to 500 microns, 500 microns or less, 400 microns or less, or 300 microns or less. The tubular channel can also be perfusable. In addition, the tubular channels can also be expandable in response to increases in pressure therein. Tubular channels can be lined with cells, including epithelial and endothelial cells. In certain aspects, the first tubular channel is lined with endothelial cells. In certain aspects, the second tubular channel is lined with epithelial cells.

The first tubular channel can also include a first tubular inlet and a first tubular outlet on the surface of the hydrogel matrix. The second tubular channel can also include a second tubular inlet and a second tubular outlet on the surface of the hydrogel matrix. The first tubular channel can include a valve or other positive feature. Tubular channels can also include spikes that extend therefrom into the hydrogel matrix. Tubular channels can be filled with any appropriate fluid or gas. Such fluids or gases can include, by way of example but not limitation, bodily fluids and oxygen. In certain aspects, the first tubular channel can be filled with a fluid. In certain other aspects, the first tubular channel can be filled with culture media, red blood cells, blood, urine, bile and/or gases such as nitrogen and/or oxygen. In certain aspects, the second tubular channel can be filled with culture media, red blood cells, blood, urine, bile and/or gases such as nitrogen and/or oxygen. Tubular channels can also be filled with one or more different fluids and/or gases.

Hydrogels of the present disclosure can include more than two tubular channels. For example, a hydrogel can include a third tubular channel and a fourth tubular channel. A tubular channel can interpenetrate more than one other tubular channel. For instance, a third tubular channel can interpenetrate a fourth tubular channel. Similarly, a second tubular channel can interpenetrate a first tubular channel and a third tubular channel. Tubular channel networks comprising multiple tubular channels may also interpenetrate at least one tubular channel or at least one other tubular channel network. For example, a third tubular channel may interpenetrate a first tubular channel that is also interpenetrated by a second tubular channel. As another example, a third tubular channel and fourth tubular channel can be interpenetrating and interpenetrate a first tubular channel or an interpenetrating network comprising a first tubular channel and a second tubular channel. In this manner, complex models can be constructed which permit complex interactions between tubular channels and tubular channel networks. The foregoing examples of multiple tubular channels are for exemplary purposes only and not intended to limit this disclosure.

Process for Manufacturing a Multi-Layer Hydrogel Matrix Construct

In certain embodiments, a process for manufacturing a multi-layer hydrogel matrix construct is provided. First, a 3D model of the multi-layer hydrogel matrix construct is created using a design software, wherein the 3D model of the multi-layer hydrogel matrix construct comprises a first computational algorithm that yields a first elongated void in the multi-layer hydrogel matrix construct providing a first tubular channel, and a second computational algorithm that yields a second elongated void in the multi-layer hydrogel matrix construct providing a second tubular channel, wherein the second computational algorithm results in the second tubular channel interpenetrating the first tubular channel. The 3D model is then converted to a format suitable for use in a 3D printing software to yield a formatted 3D model. The formatted 3D model is then imported into the 3D printing software, wherein the 3D printing software is programmed to slice the 3D model into multiple two-dimensional (2D) xy images. A prepolymerization solution is supplied to a vat associated with a build platform of a 3D printer, wherein the vat is transparent, and wherein the prepolymerization solution comprises a photosensitive polymer having a molecular weight of greater than 2,000 Daltons and at least two vinyl groups per molecule of polymer, a light-absorbing additive material to control light penetration, and a photoinitiator. The vat can also include a coating to which the hydrogel will not adhere such as a hydrophobic coating. For example, the coating can be polydimethylsiloxane (PDMS). This allows the hydrogel to separate from the vat without sticking. A mobile Z-axis stage of the 3D printer is positioned at a distance from the vat, wherein the Z-axis stage includes a surface sufficient for gelled material to adhere thereto, wherein the distance between the surface and an inner bottom surface of the vat is equivalent to a desired layer thickness of the tissue construct. A pattern is then projected on the inner bottom surface of the vat. For example, a light source may be projected through an optical configuration such as a DLP system, to produce the pattern. A layer of the multi-layer hydrogel matrix construct is then polymerized. The steps of supplying a prepolymerization solution, positioning the mobile Z-axis stage, projecting the light source and polymerizing a layer can be repeated one or more times, wherein the mobile Z-axis stage is moved so that the distance moved is equivalent to the desired thickness of each subsequent layer, and wherein the same or a different pattern is displayed for each subsequent layer. In certain aspects, at least the steps of supplying a prepolymerization solution to a vat, positioning a mobile Z-axis stage, projecting a light source through an optical configuration, and polymerizing a layer of the multi-layer tissue construct are performed under hypothermic conditions. The hypothermic conditions can include a temperature of 4° C. The optical configuration can include a collimator, a condenser, filters, and a DMD array. For example, the optical configuration can be part of a digital light processing system.

In certain aspects, the distance is from 50 microns to 100 microns. In certain other aspects, the distance is 50 microns. The optical configuration can include a mirror, wherein the mirror is positioned to provide the pattern on the inner bottom surface of the vat. The mirror can be slid back and forth to center the projection and provide for alignment of the layers of the multi-layer hydrogel matrix construct.

In some embodiments, the repeating step is performed at least once to produce a second layer, wherein the prepolymerization solution used for the second layer comprises a second photosensitive polymer that is different from the photosensitive polymer used to fabricate the first layer. In certain aspects, the second photosensitive polymer can have a different molecular weight from the photosensitive polymer. The repeating step can be performed a number of times sufficient to yield the multi-layered hydrogel matrix construct having the first tubular channel and the second tubular channel.

Figure 27:
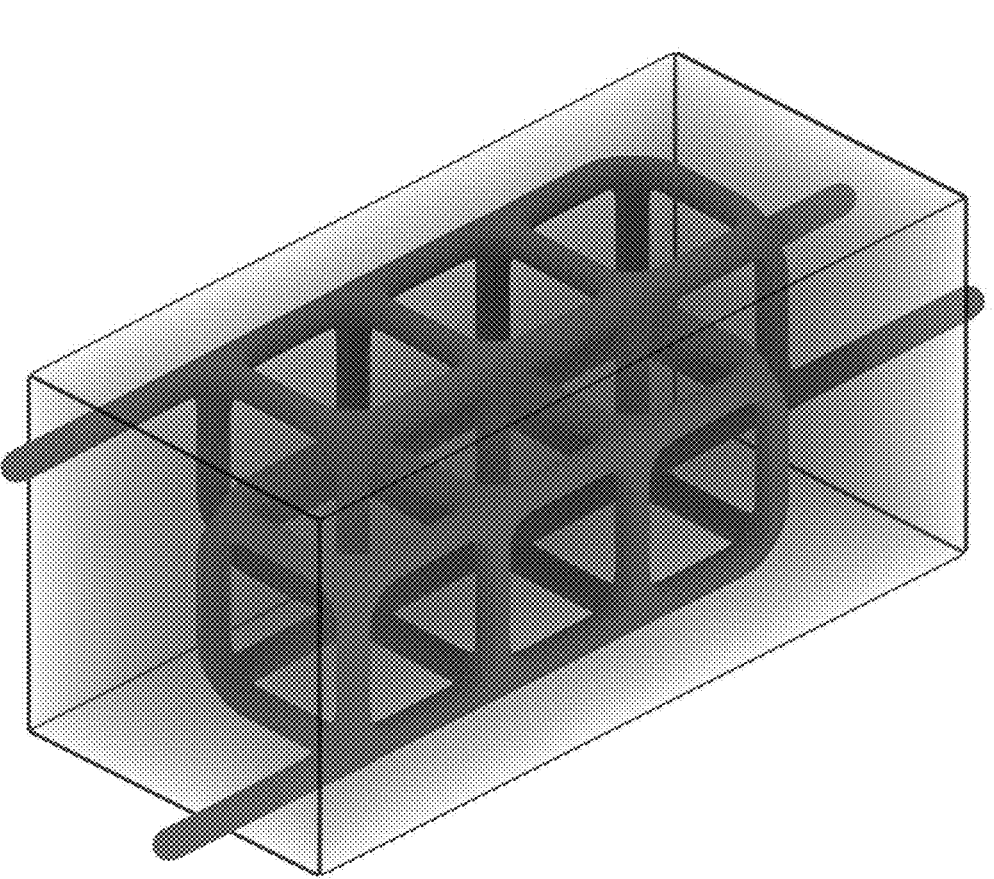
FIG. 27 depicts an intercalated Plumber's Nightmare model with two tubular channels that interpenetrate.

In certain embodiments, the first computational algorithm can be derived from knot theory. In certain aspects, the first computational algorithm and/or the second computational algorithm can be a Hilbert curve. The first computational algorithm and second computational algorithm can conform to Murray's Law. In certain aspects, the first computational algorithm can result in the first tubular channel being branched. The first computational algorithm and the second computational algorithm can include a mathematical space-filling model. The mathematical space-filling model can include the Plumber's Nightmare, Peano curve, Hilbert curve, Pythagoras tree, and Brownian tree models. FIG. 27 shows an intercalated Plumber's Nightmare model with two separate channels that interpenetrate.

The assembled 3D printer is an automated, computer-aided 3D prototyping device which utilizes additive manufacturing to selectively pattern photosensitive biomaterials one layer at a time, yielding a 3D tissue engineered construct. The printer contains a mobile Z-axis stage that is lowered onto the build platform which contains a vat with the prepolymerization solution containing photosensitive polymers and a photoinitiator. Attached to the Z-axis stage is a surface onto which the gelled material adheres to. Additionally, the base of the printer houses a 45 degree mirror which reflects a horizontal projection onto the inner bottom surface of the transparent vat. The assembled printer also houses microelectronics that automate the printing process.

Figure 23:
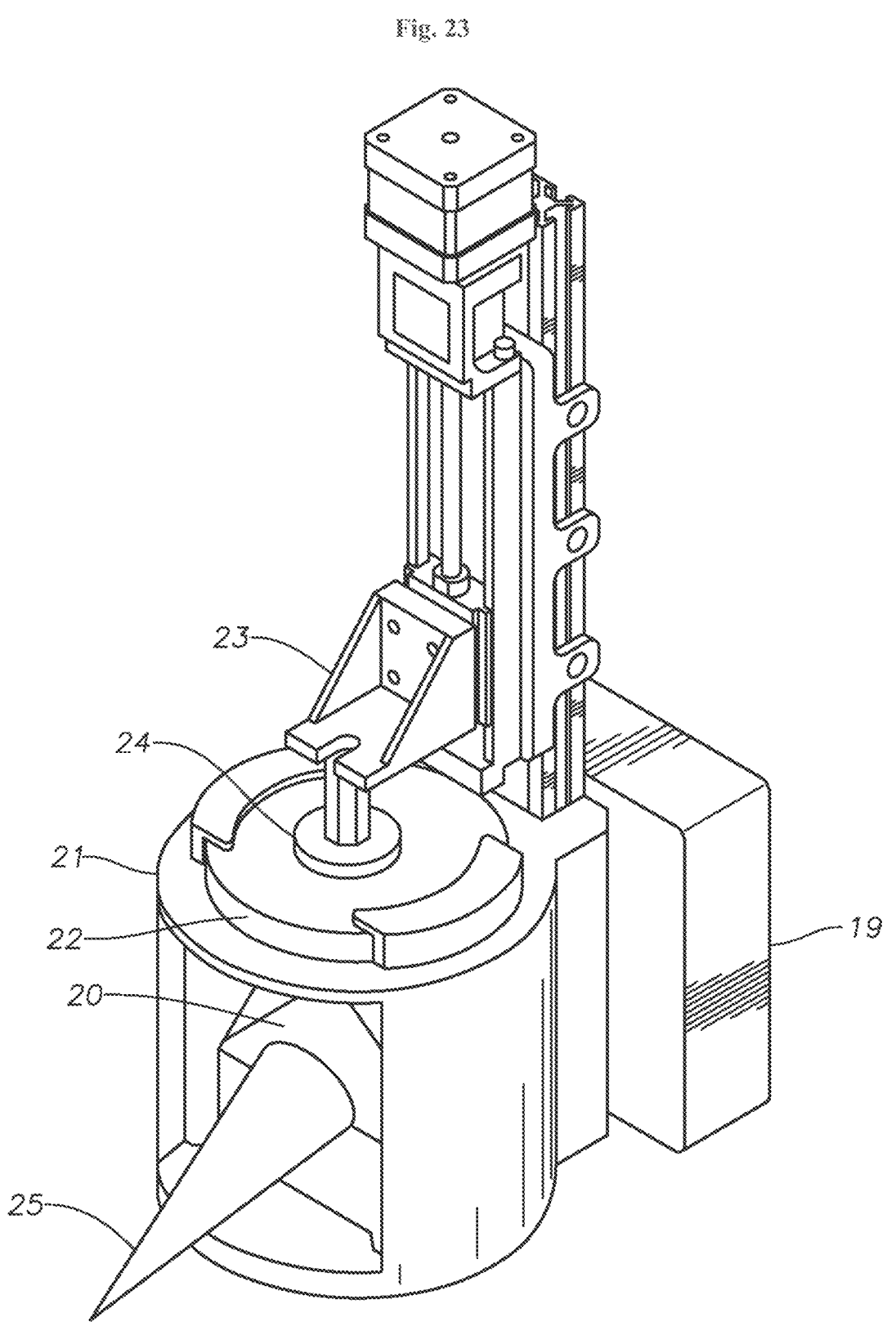
FIG. 23 depicts a 3D printer of the present disclosure.

A 3D bioprinter of the present disclosure is shown in FIG. 23. The 3D printer includes a frame 19 which includes a mirror 20, a build platform 21, a vat 22, a mobile Z-axis stage 23 with a surface for the hydrogel to adhere to 24. In operation a projected pattern 25 produced by projecting a light source through an optical configuration is projected onto the mirror 20 which then reflects the image onto the inner bottom surface of the vat 22.

In order to print structures, a 3D model is created in computer aided design (CAD) software and then exported to stereolithography (.stl) format. The .stl file is imported into software in which printing parameters are input. Then, the software computationally slices the 3D model into two-dimensional (2D) xy images, which act as dynamic photo-masks, and uses the inputted print parameters to create commands for controlled automated printing. Once the transparent vat is filled with prepolymerization mixture, the Z-axis stage is lowered onto the vat so that the distance between the surface and the inner bottom surface of the vat is the desired layer thickness. Then, a light source projects light through an optical setup containing a combination of collimator, condenser, filters such as dichroic or bandpass to select specific wavelengths of interest, and a DMD array, such as a commercially available projector or a pico-pro-jector, resulting in a pattern (the first layer of the 3D model), on the inner bottom surface of the vat, yielding a specific 3D patterned layer. After the material undergoes gelation, the Z-axis stage automatically moves up to the next layer height and the process is automatically continues with successive, automated projection/Z-axis stage movement until the final 3D construct is obtained.

Figure 4A:
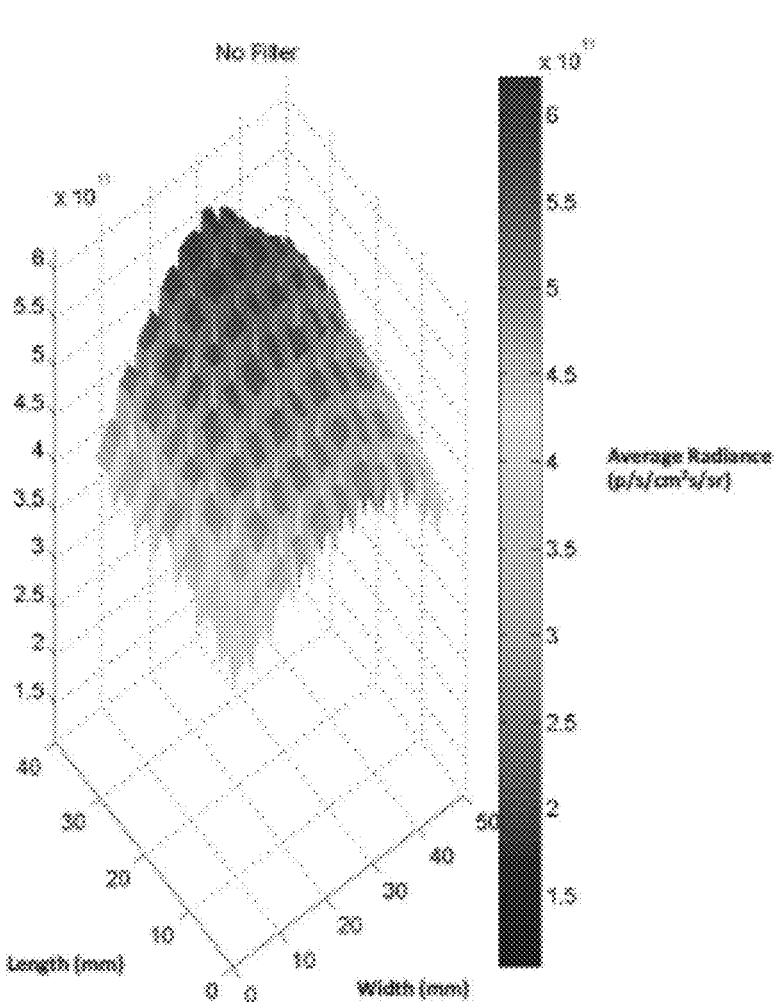
FIG. 4A depicts the power output of a projector as measured by radiance using phosphor film.
Figure 4B:
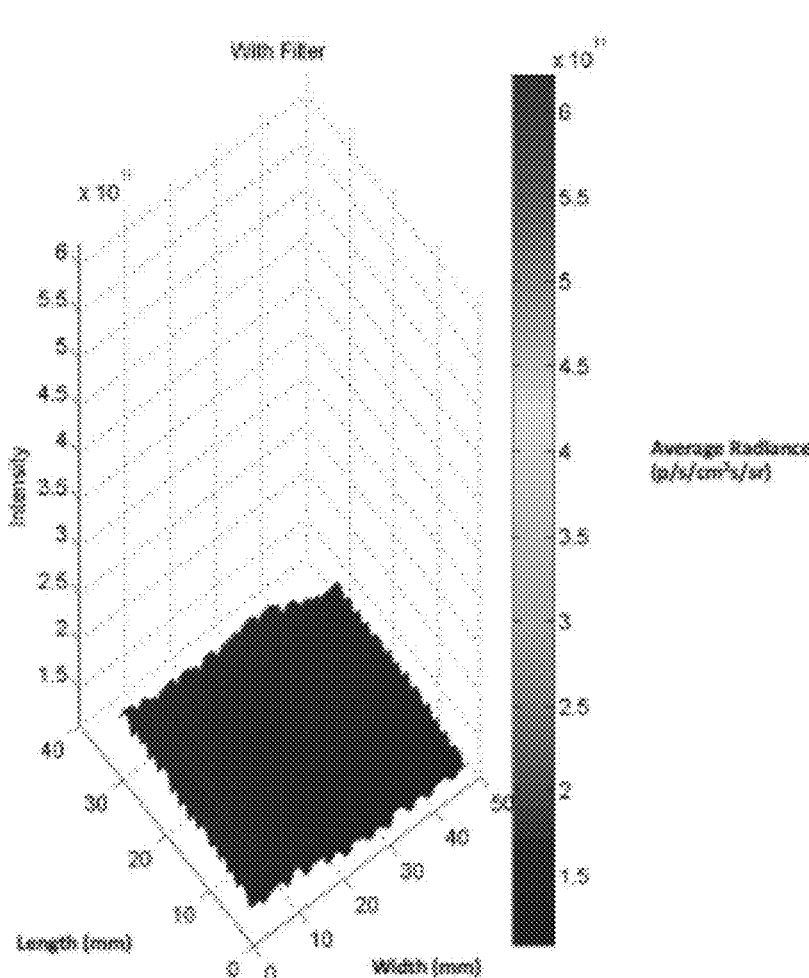
FIG. 4B depicts the power output of a projector to which flat-fielding was applied as measured by randiance using phosphor film.

Additionally, we realize that the power output from pro-jector devices may not be homogenous. Thus, we have also devised a manner to homogenize power output, or flat-field, so that the projected pattern does not have unintentional heterogenous properties. To this end, we projected a blank exposure onto a film of phosphors and then obtained a luminescent image. This image contains a 2D matrix of intensity values that are essentially normalized and inverted in numerical computing programs, such as MATLAB. The inverted image essentially acts as a filter, resulting in a more homogenous power output to ensure that the gelation of materials is homogenous throughout the whole projected layer (see FIGS. 4A and 4B).

Modifications to this assembly can involve addition of a syringe setup to automatically dispense more prepolymer-ization solution during the printing process, as necessary. To achieve more heterogenous constructs with different mate-rials, a modification to the assembly involves modifying the build platform, vat, and/or the Z-axis stage so that multiple materials can be automatically printed with this technique. For example, the build platform can be designed in such a way as to house multiple vats with different materials for printing 3D hydrogels with multiple materials.

Multiscale, branched vascular network with an interpen-etrated airway network can be fabricated by using the bioprinter in its basic configuration. This model is prepared in CAD software and then exported into an .stl format. The exported file is uploaded to a software and the print param-eters are entered. Once the prepolymerization solution is prepared, it is transferred onto the vat housed on the build platform. Then, the Z-axis stage is lowered to obtain the desired layer thickness. A series of automated projections of the 3D model and Z-stage translations ultimately results in the final 3D printed hydrogel. The 3D bioprinted hydrogel can then be removed from the Z-platform. The vascular channel of the 3D printed model can be endothelialized by perfusion of endothelial cells while the airway channel can be epithelialized by perfusion of epithelial cells. The vas-cular network serves as the blood supply, delivering oxygen and nutrients to the cells in the bulk of the hydrogel while the airway network provides a means to supply oxygen to the vascular network (see FIGS. 5 and 10).

Figure 5:
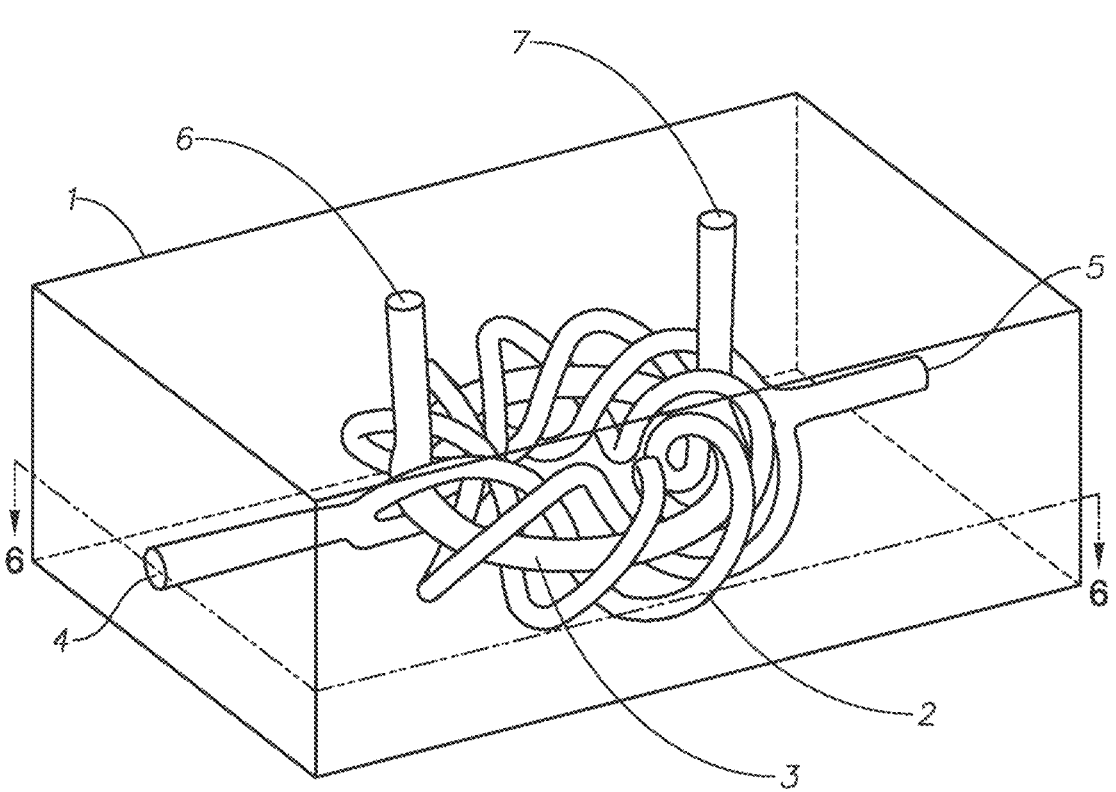
FIG. 5 depicts a hydrogel containing a first tubular channel and a second tubular channel wherein the second tubular channel interpenetrates the first tubular channel but the first and second tubular channels do not intersect.
Figure 6:
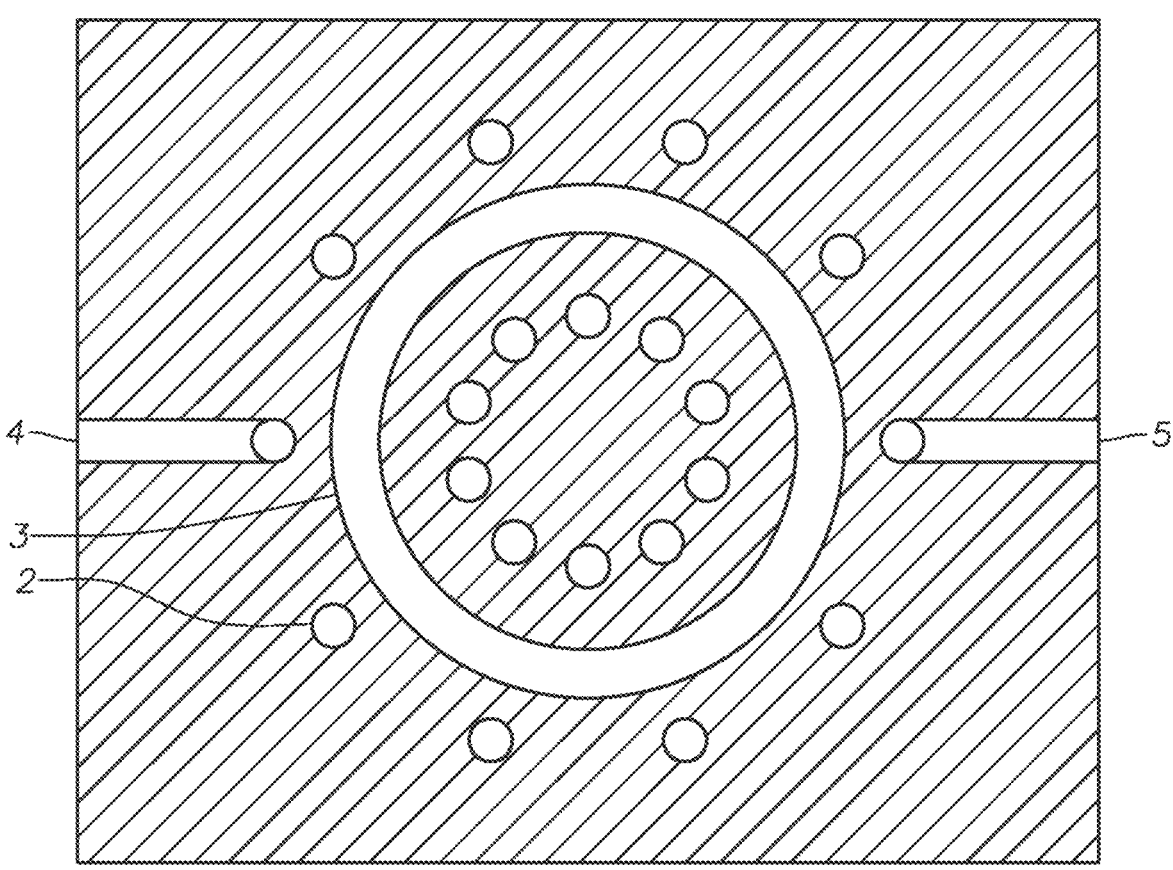
FIG. 6 depicts a cross-section of the hydrogel of FIG. 5 showing the circular cross-sections of the first tubular channel and the second tubular channel.
Figure 7:
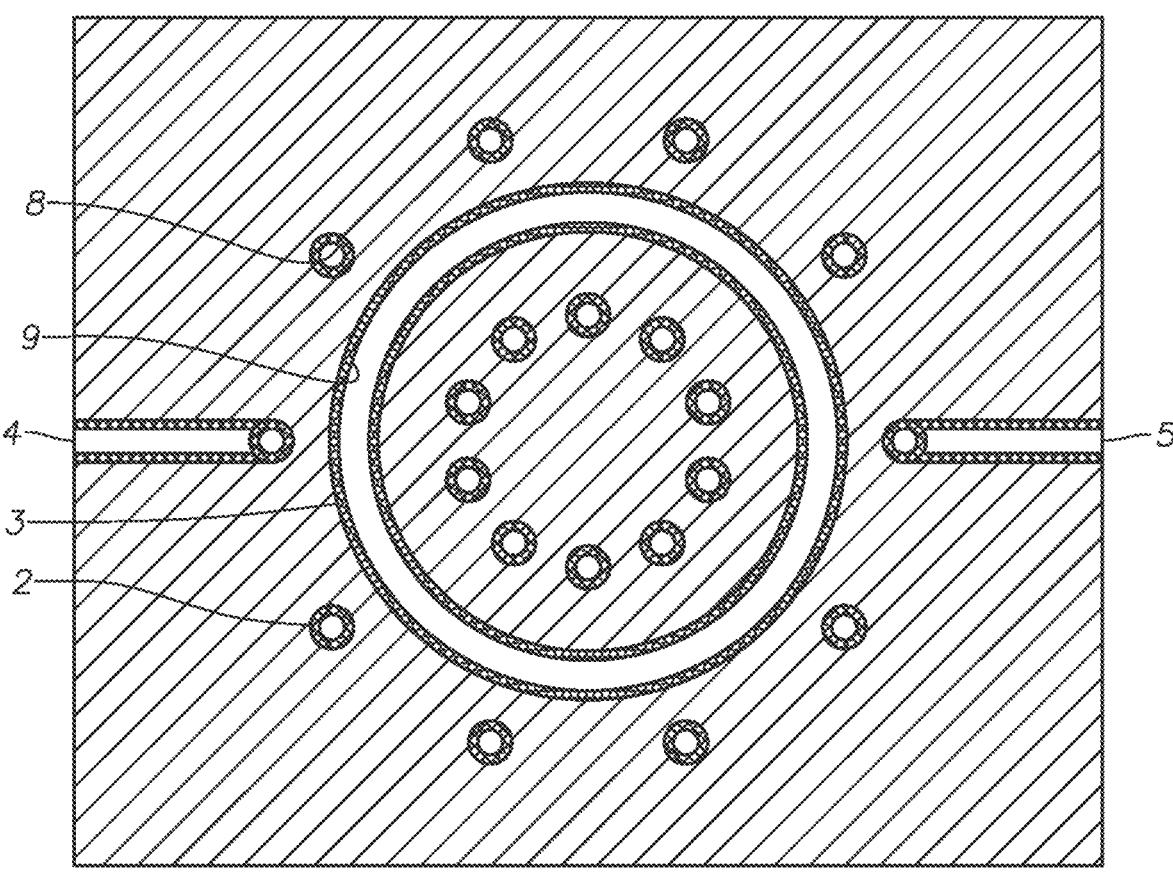
FIG. 7 depicts a cross-section of the hydrogel of FIG. 5 with cells lining the first tubular channel and the second tubular channel.
Figure 8A:
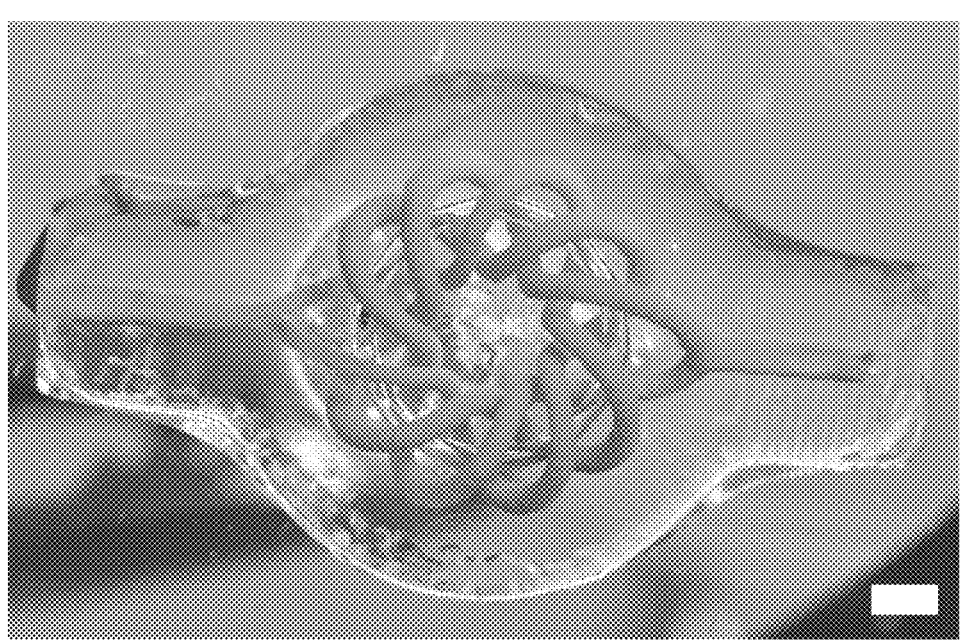
FIG. 8A includes a photograph of a hydrogel as depicted in FIG. 5 with the spiral channel casted with red MICRO-FIL® and an open airway channel. Scale bar=2 mm.
Figure 8B:
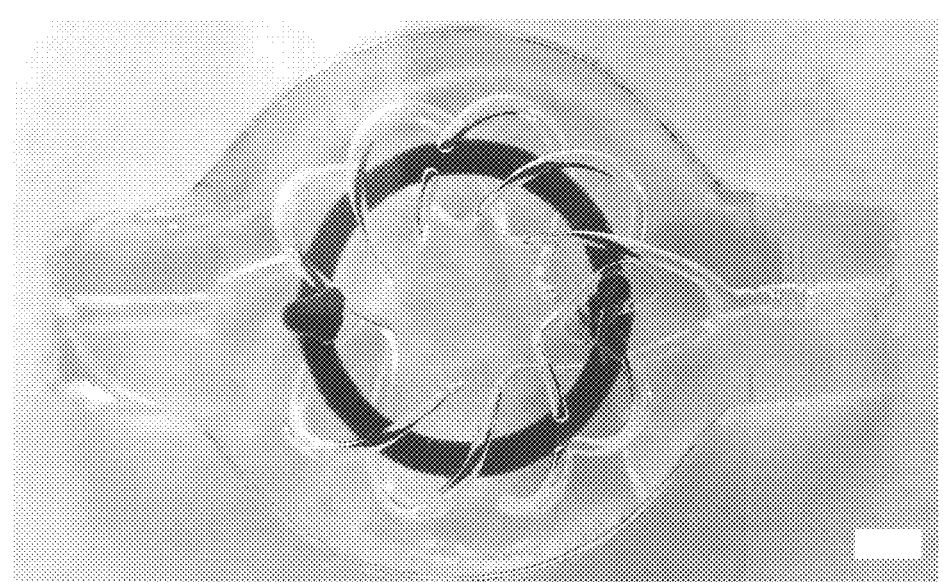
FIG. 8B includes a photograph of a hydrogel as depicted in FIG. 5 with the airway channel coasted with blue MICROFIL® and an open arterial channel. Scale bar=2 mm.
Figure 9A:
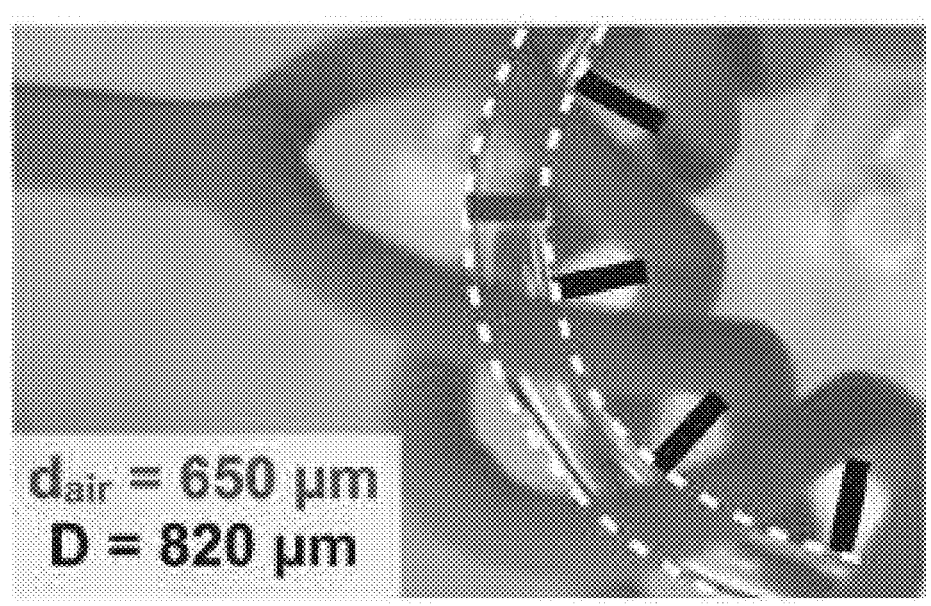
FIG. 9A is a close-up of the resting airway of a hydrogel of the design shown in FIG. 5.
Figure 9B:
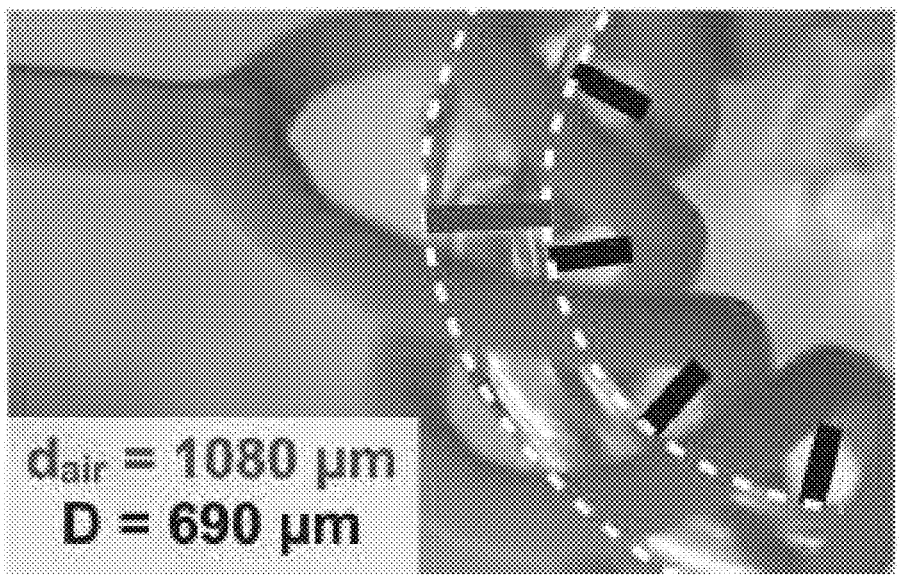
FIG. 9B is a close-up of the inflated airway of a hydrogel of the design shown in FIG. 5.
Figure 11:
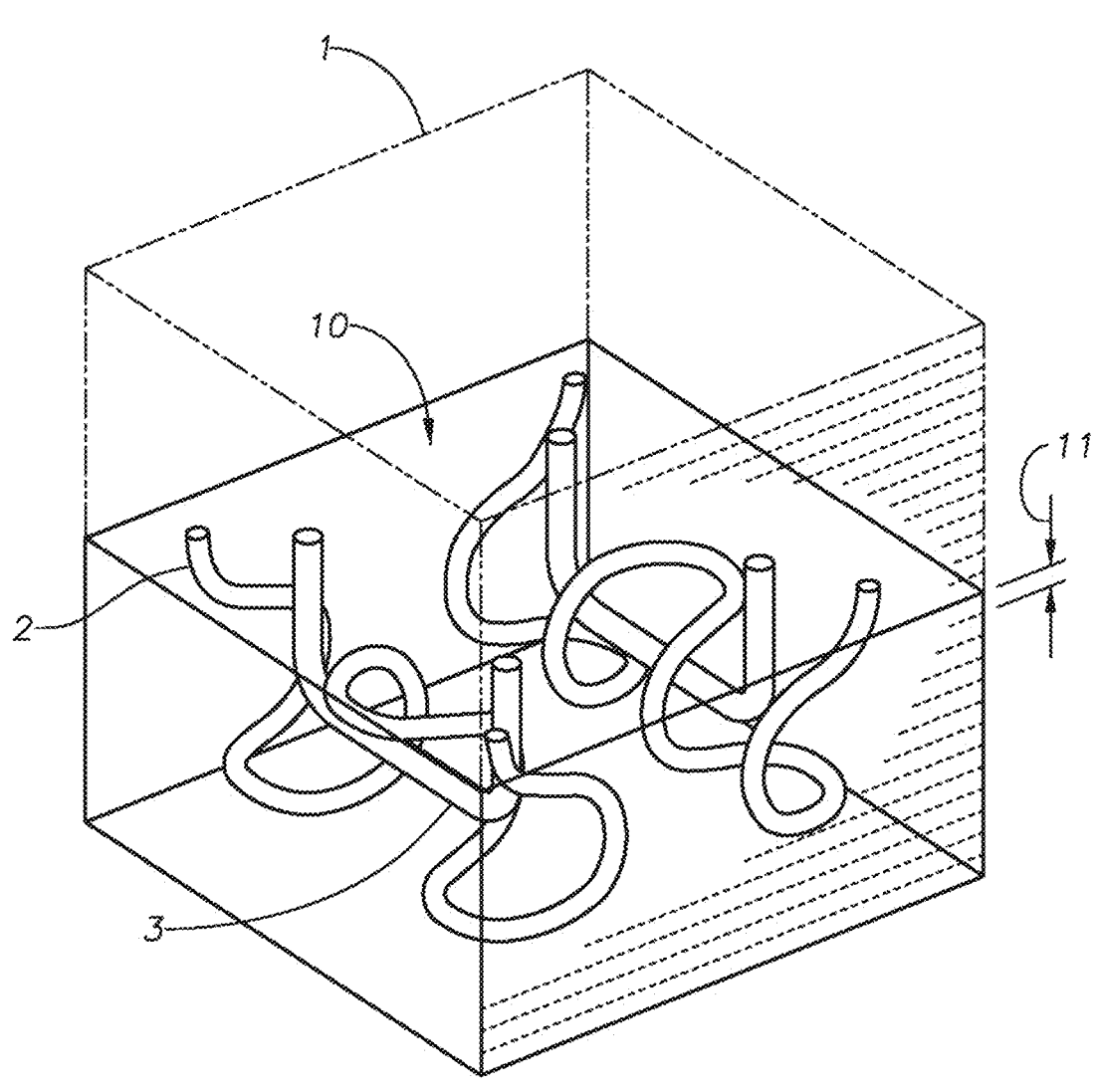
FIG. 11 depicts the hydrogel of FIG. 10 showing the printed layers of the construct.
Figure 12:
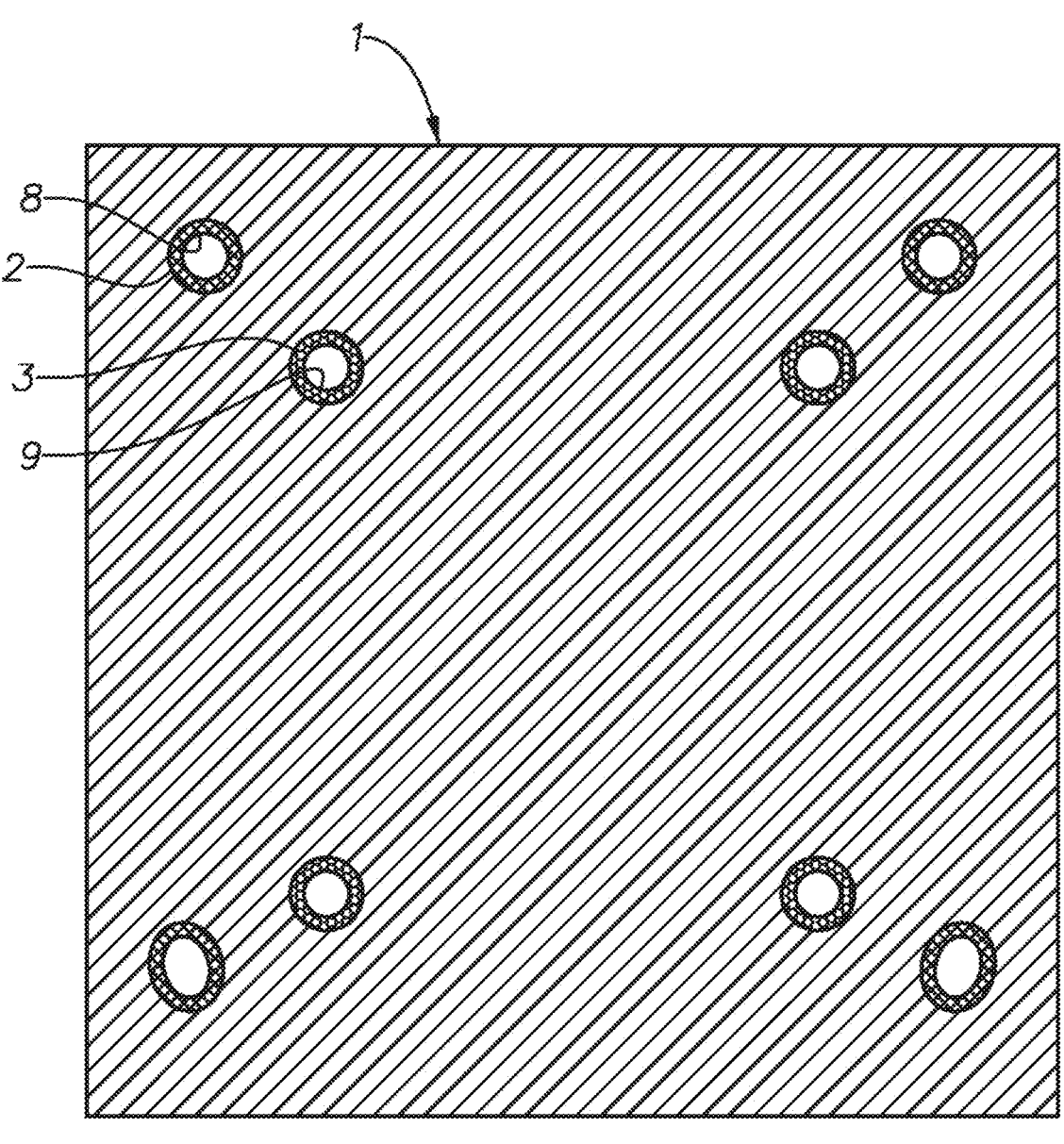
FIG. 12 depicts a cross-section of the hydrogel of FIG. 10 with cells lining the first tubular channel and the second tubular channel.
Figure 13A:
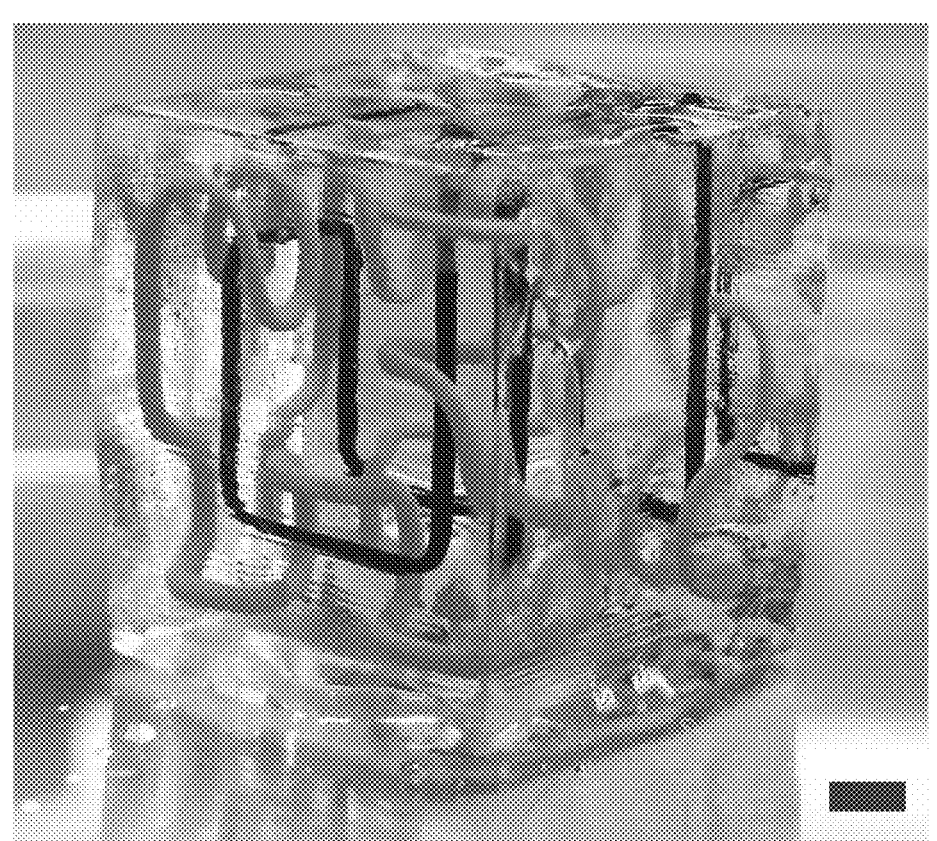
FIG. 13A includes a photograph of a hydrogel as depicted in FIG. 10 with the arterial channel casted in red MICRO-FIL® and the airway channel casted with blue MICRO-FIL®. Scale bar=3 mm.
Figure 13B:
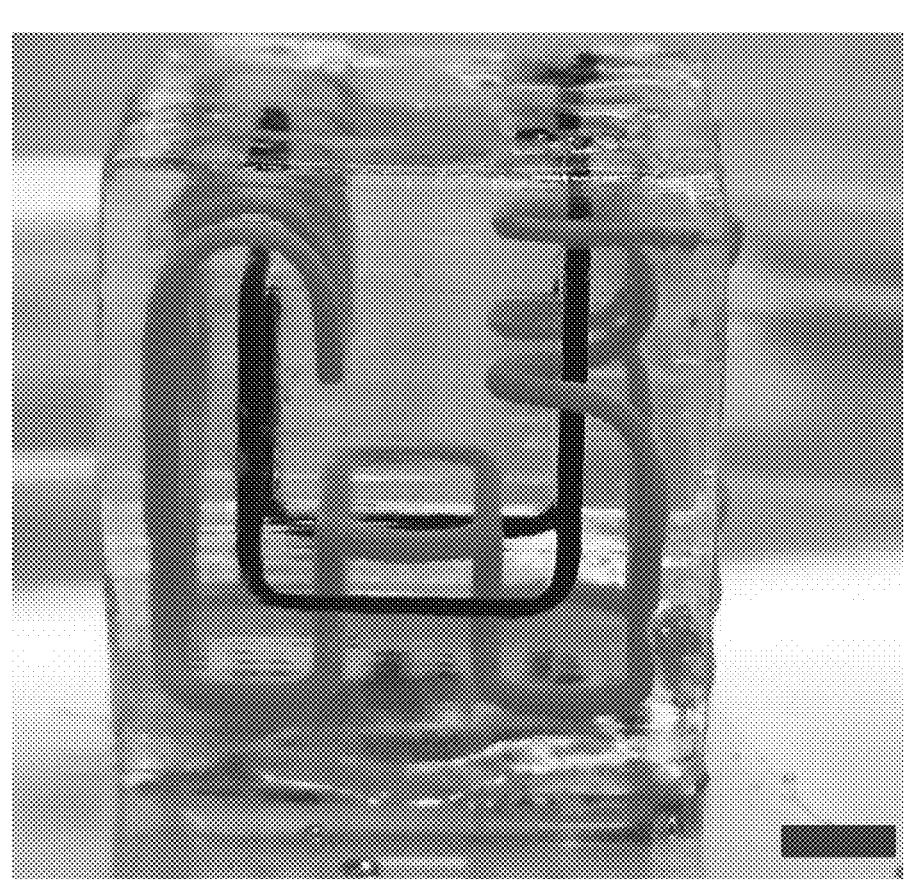
FIG. 13B includes a photograph of a hydrogel as depicted in FIG. 10 with the arterial channel casted in red MICRO-FIL® and the airway channel casted with blue MICRO-FIL®. Scale bar=3 mm.

The first tubular channel and the second tubular channel can both have circular cross-sections (see FIGS. 6 and 11) and can have cells lining the channel lumens (see FIGS. 7 and 12). The hydrogel can be printed such that the arterial channel and airway channel interpenetrate (see FIGS. 8A-8B and 13A-13B). The specific model of FIG. 5 is intended for lung applications and, interestingly, we observe that the printed hydrogel is compliant and the airway chan-nels are able to expand in volume once they are inflated (see FIGS. 9A and 9B).

Figure 14:
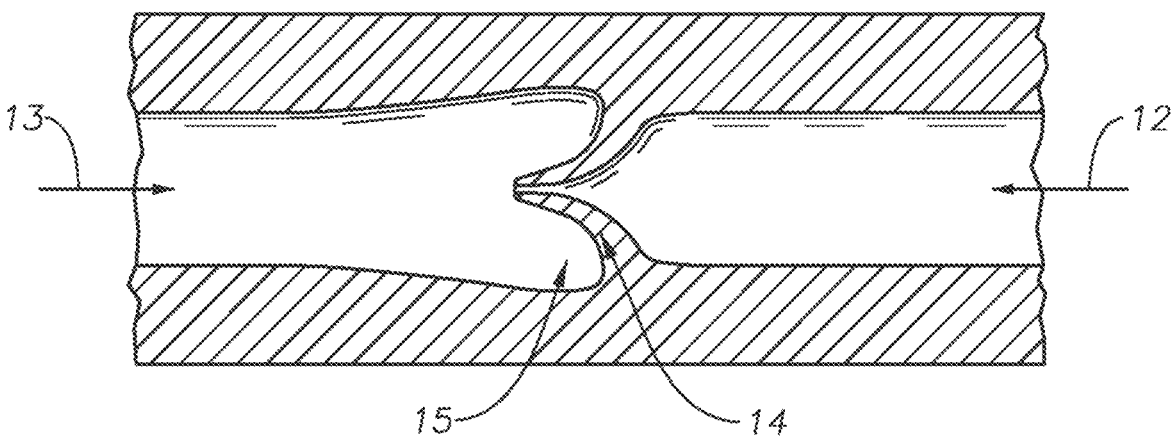
FIG. 14 depicts a cross-section of a perfusable 3D model containing a valve.
Figure 15:
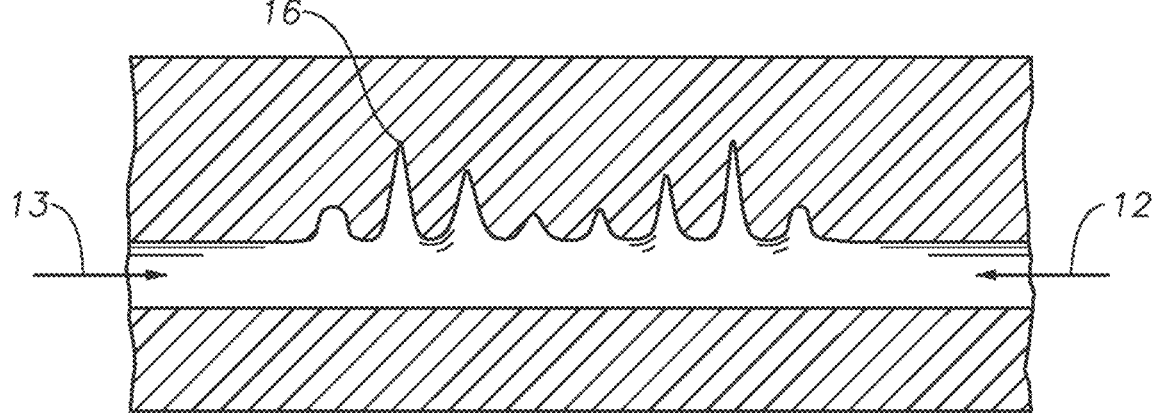
FIG. 15 depicts a cross-section of a perfusable 3D model containing spikes.
Figure 16:
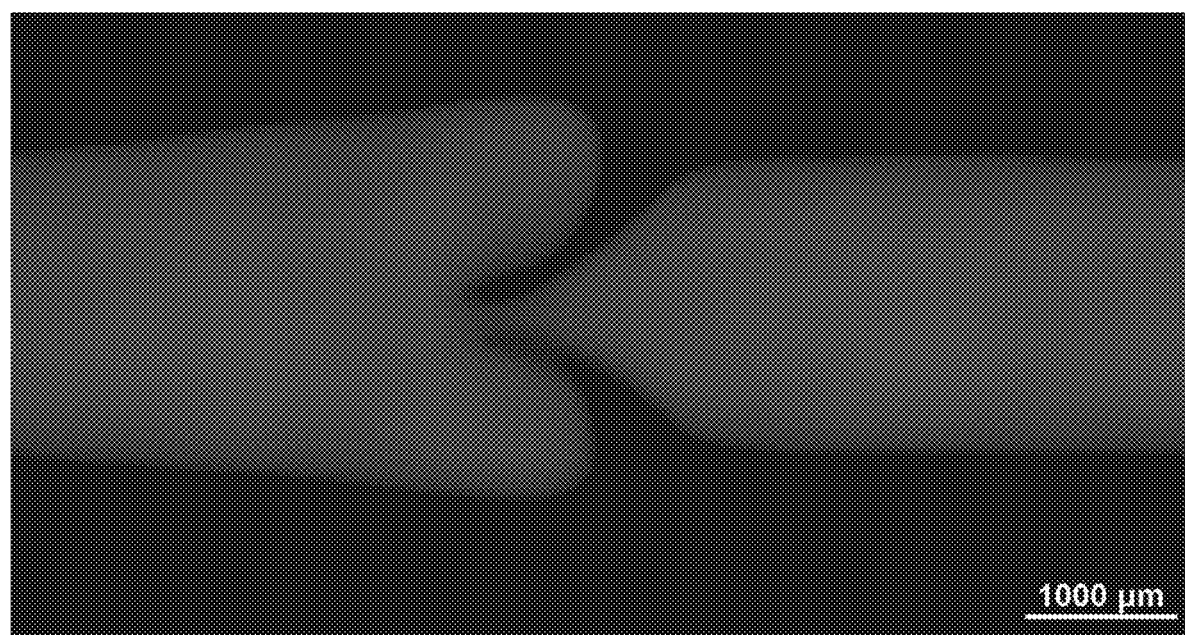
FIG. 16 includes a fluorescent micrograph of fluorescent media inside a printed valve model. Scale bar=1 mm.
Figure 17:
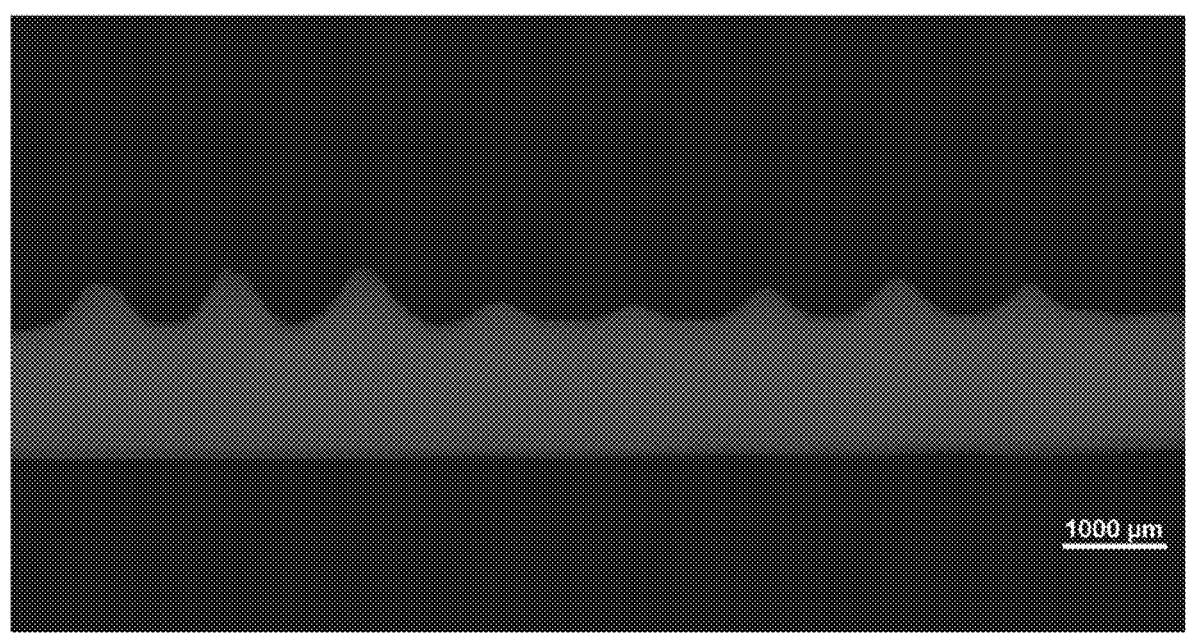
FIG. 17 includes a fluorescent micrograph of fluorescent media inside a printed spike/thorn model. Scale bar=1 mm.

The tubular channels can include a valve (see FIGS. 14 and 16) and/or spikes which are negative features that penetrate into the hydrogel (see FIGS. 15 and 17). The valve can mimic a bicuspid valve by ensuring efficient unidirec-tional transport of fluid. The valve can open and permit the flow of fluid when the pressure at the valve inlet is larger than the valve outlet. The valve remains open when the pressure at the inlet and outlet are equal. However, once the pressure of the inlet is less than that of the outlet, the valve closes, blocking the backflow of fluid through the leaflets. Negative features, such as spikes which have sharp tips can be exploited to control the spatial sprouting of seeded endothelial cells into the bulk hydrogel region.

In FIG. 14, the inlet of the tubular channel 12 allows fluid to flow through the valve toward the outlet 13. If the pressure is too low, the leaflets 14 will close around the sinus 15, effectively preventing the backflow of fluid. In FIG. 15, the inlet 12 allows fluid to flow through the tubular channel toward the outlet 13. However, the negative features, in this case spikes 16 may assist in the spatial sprouting of endothe-lial cells in the tubular channel.

Figure 18:
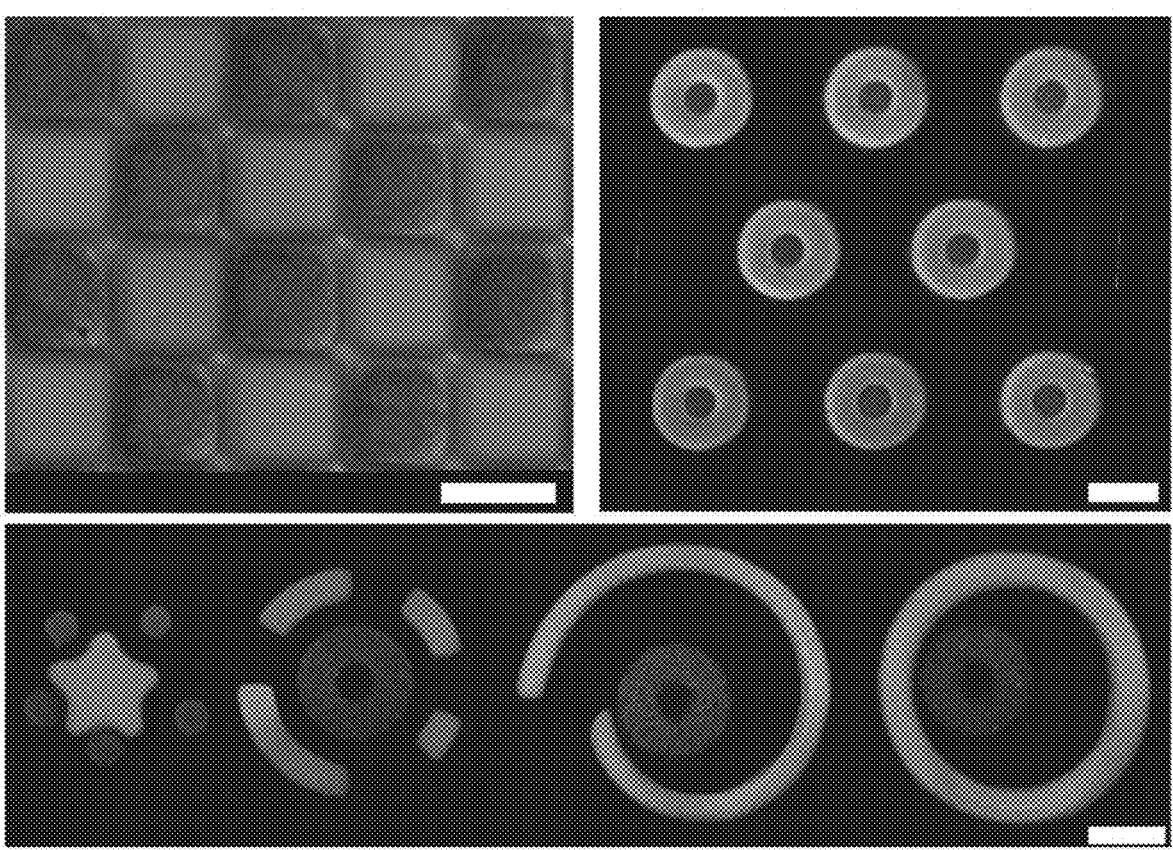
FIG. 18 includes a fluorescent micrograph of patterns printed using a PEGDA prepolymerization solution containing either fluorescent microbeads or FITC-Dextran. Scale bar=1 mm.

Multi-layered vascular tubes consisting of an outer layer of fibroblasts, an inner layer of smooth muscle cells, and endothelialized lumen can be fabricated by using the bio-printer in a configuration that allows printing with multiple materials. Fibroblasts, smooth muscle cells, and endothelial cells are cultured separately with appropriate culture condi-tions. The fibroblast cells and smooth muscle cells are individually mixed at desired densities with the prepolymer-ization solution containing photopolymer and photoinitiator. Then, the prepolymerization solution, containing cells, is deposited in vat(s) on the build platform. Additionally, the build platform contains a vat with an acellular prepolymer-ization mixture that will be used to print the base of the 3D model. The Z-axis stage is lowered into the acellular pre-polymerization mixture at the desired layer thickness, and the printing process is initiated. Once sufficient base layers are printed, the Z-axis stage retracts from the base vat and is lowered into the position of the second material, contain-ing the prepolymerization mixture with smooth muscle cells, at the next layer height. After gelation of that layer, the Z-axis stage moves out of the second vat, is rinsed with an acellular prepolymerization mixture to reduce contamina-tion, and is lowered into the third vat, containing the prepolymerization mixture with fibroblast cells, at the same layer height as the previous projection. After this layer is gelled, the resultant layer consists of a pattern with 2 different cell types. The printing of two different materials in a patterned layer can be seen in FIG. 18 which shows printing with two different prepolymerization solutions with two different fluorophores, respectively. The Z-axis stage moves out of the third vat, is rinsed, and moves back to the second vat and the process is repeated until the final mul-tilayered, multi-material 3D hydrogel is bioprinted. The 3D bioprinted hydrogel is then removed, and endothelialized by perfusing the channel with endothelial cells.

Mathematical Fractal Space-filling Models

Mathematical fractal space-filling models of the present disclosure can include, but are not limited to, the Plumber's Nightmare, Peano curve, Hilbert curve, Pythagoras tree, and Brownian tree models. Such models may be intercalated to allow for interpenetration of the tubular structures enabling perfusion between the tubular structures. Knot theory describes the way in which a circle can be embedded in three dimensions. A special kind of knot, a torus knot, lies on the surface of an unknotted torus. These knots are specified by a pair of coprime integers p and q. Essentially, q refers to the number of times a knot winds around a circle in the interior of the torus while p refers to the number of revolutions before joining its ends. If p and q are not relatively prime, then a torus link with more than one continuous component is obtained. FIG. 5 includes a (3,10) torus knot that has branched connections at either end to provide an inlet and an outlet. Such a model can allow for a spiral lung model. In FIG. 5, the hydrogel 1 contains a first tubular channel 2 and a second tubular channel 3. The first tubular channel has an inlet 4 and an outlet 5. The second tubular channel has an inlet 6 and an outlet 7. The first tubular channel 2 and second tubular channel 3 do not intersect but are interpenetrating. FIG. 6 shows a cross-section of the hydrogel of FIG. 5 drawn at a line 6 where the first tubular channel 2 has a circular cross-section and the second tubular channel 3 also has a circular cross-section. FIG. 7 shows a cross-section of the hydrogel of FIG. 5 where a first cell type 8 lines the first tubular channel and a second cell type 9 lines the second tubular channel.

Figure 10:
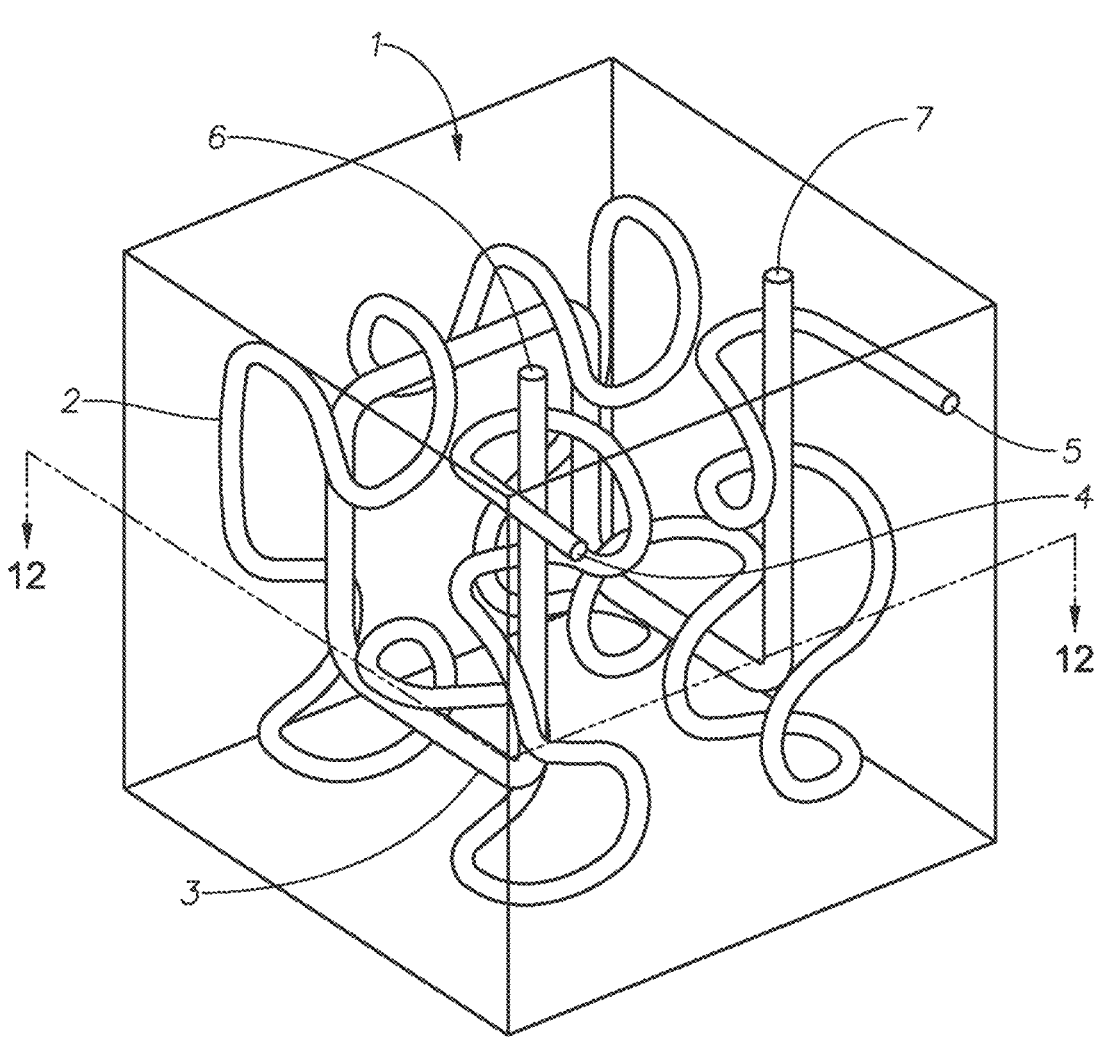
FIG. 10 depicts a hydrogel containing a first tubular channel and a second tubular channel wherein the second tubular channel interpenetrates the first tubular channel but the first and second tubular channels do not intersect.

Another space filling model involves the Hilbert Curve. Hilbert curves are continuous fractal space filling structures that fill a plane without leaving gaps. The basic clement in this self-similar curve is the U-shape. From this basic shape, higher order curves can be obtained sequentially by a recursive process of replication and linking. This is achieved by distributing four shrunken copies of the curve to the four quadrants of a square plane followed by reorientation of the copies so that the end of the curve in one quadrant lines up with the beginning of the curve in the next quadrant. Line segments are then drawn to connect the four quadrants into a single curve. A 3D analog of the Hilbert curve can be generated to fill the volume of a cube using the same principles as above. FIG. 10 includes a (1,2) Hilbert curve model with a first order Hilbert curve and an interpenetrating second order Hilbert curve. In certain embodiments, the second order curve can allow for arterial flow while the first order curve can allow for airway flow. In FIG. 10, the hydrogel 1 contains a first tubular channel 2 and a second tubular channel 3. The first tubular channel has an inlet 4 and an outlet 5. The second tubular channel has an inlet 6 and an outlet 7. The first tubular channel and second tubular channel do not intersect but are interpenetrating. FIG. 11 shows the layers 11 of the hydrogel construct of FIG. 10. FIG. 12 shows a cross-section of the hydrogel of FIG. 10 drawn at a line 12 indicated in FIG. 10 where a first cell type 8 lines the first tubular channel 2 and a second cell type 9 lines the second tubular channel 3.

The Lindenmayer system (L-system) is a language composed of a set of strings with specific rules. The L-system consists of two components: an axiom, the starting point, and a set of productions, the system rules. Application of the rules results in production of strings in the language of the L-system. Because the L-system is recursive in nature, the rules set in this system result in self-similarity, and, thus, fractal-like geometries can be obtained. Hence, the Lindenmayer system can be utilized to develop 3D constructs with control of branch geometry to obtain a vascular network in which sufficient nutrient delivery into the bulk of thick scaffolds can be achieved. Then, the L-system can be utilized again, in the same model, to obtain a parameter controlled interpenetrating airway network for delivery of oxygen.

To facilitate a better understanding of the present invention, the following examples of certain aspects of some embodiments are given. In no way should the following examples be read to limit, or define, the entire scope of the invention.

EXAMPLES

The following Examples are given to facilitate a better understanding of the printing process of the present disclosure and the specific embodiments discussed herein should not be construed as limiting the scope of the invention described herein.

Figure 19:
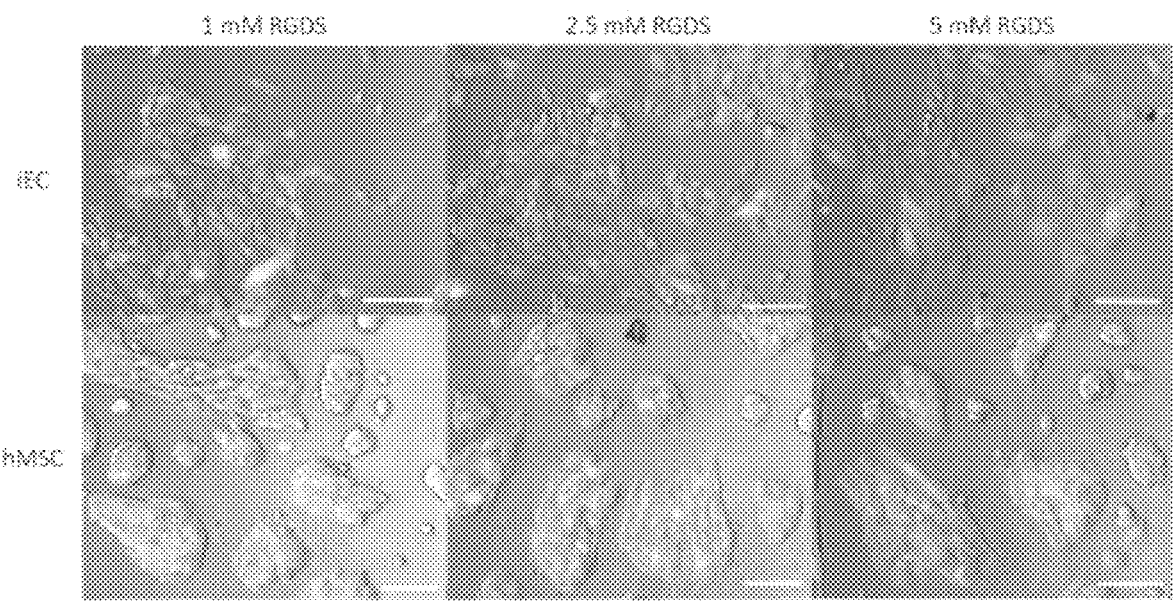
FIG. 19 includes a fluorescent micrograph of hMSC and iEC cells printed on PEGDA hydrogels containing acryloyl-PEG-CGRGDS 17 hours post-seeding. Scale bar=100 μm.

Example 1: Cell Adhesion on PEGDA Hydrogels with Acryloyl-PEG-CGRGDS hMSCs and iEC cells were seeded on PEGDA hydrogels containing varying concentrations (1 mM, 2.5 mM and 5 mM) acryloyl-PEG-CGRGDS. Both cell types demonstrated cell adhesion and cell spreading after overnight incubation (see FIG. 19). hMSC cells appeared to form cell islands with a slightly rounded morphology. Both cell types were transduced to express H2B-mCherry-CMV-EGFP-IRES-Puro. Expression of H2B-mCherry is localized to the cell nucleus while expression of EGFP is localized to the cytoplasm.

Example 2: DLP Printing of hMSCs

Figure 20:
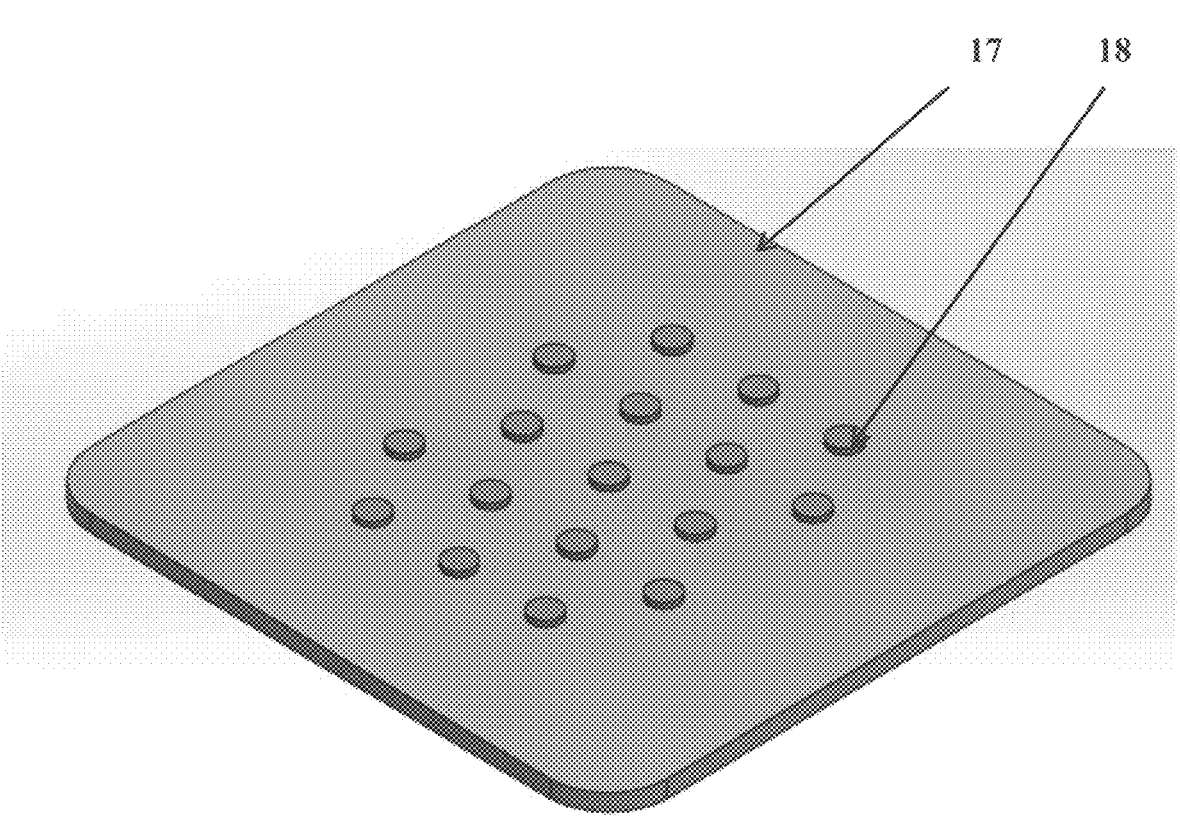
FIG. 20 depicts a hexagonal print design for printing hydrogel posts containing human mesenchymal stem cells (hMSCs) onto a support.

Three solid base layers of a prepolymerization solution comprising 15 wt % PEGDA (non-degradable) was printed as a platform 17 (see FIG. 20).

After printing the three solid base layers, human mesenchymal stem cells (hMSCs) were added to a prepolymerization solution comprising 10 wt % PEG-HD and 1% lithium acylphosphinate and printed onto the platform in a hexagonal pattern 18 (see FIG. 20) using a 3D bioprinter of the present disclosure.

Figure 21A:
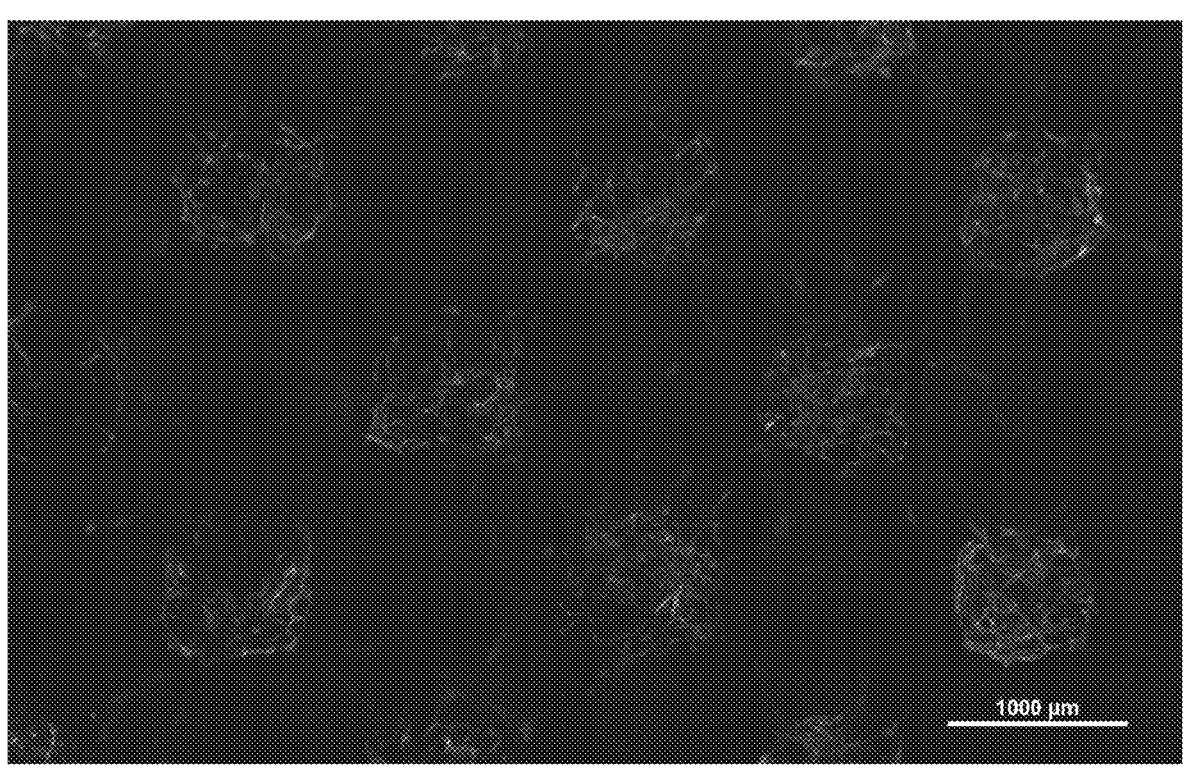
FIG. 21A includes a photograph of the hydrogel posts depicted in FIG. 20 printed using PEGDA and hMSCs wherein the cells are constitutively expressing green fluorescent protein (GFP) in the cytoplasm and H2B-mCherry (red) in the nucleus. Scale bar=1 mm.

The cells, expressing EGFP localized in the cytoplasm and H2B-mCherry in the nuclei, were imaged by aerial scans of phase and fluorescent scans as shown in FIG. 21A.

Figure 21B:
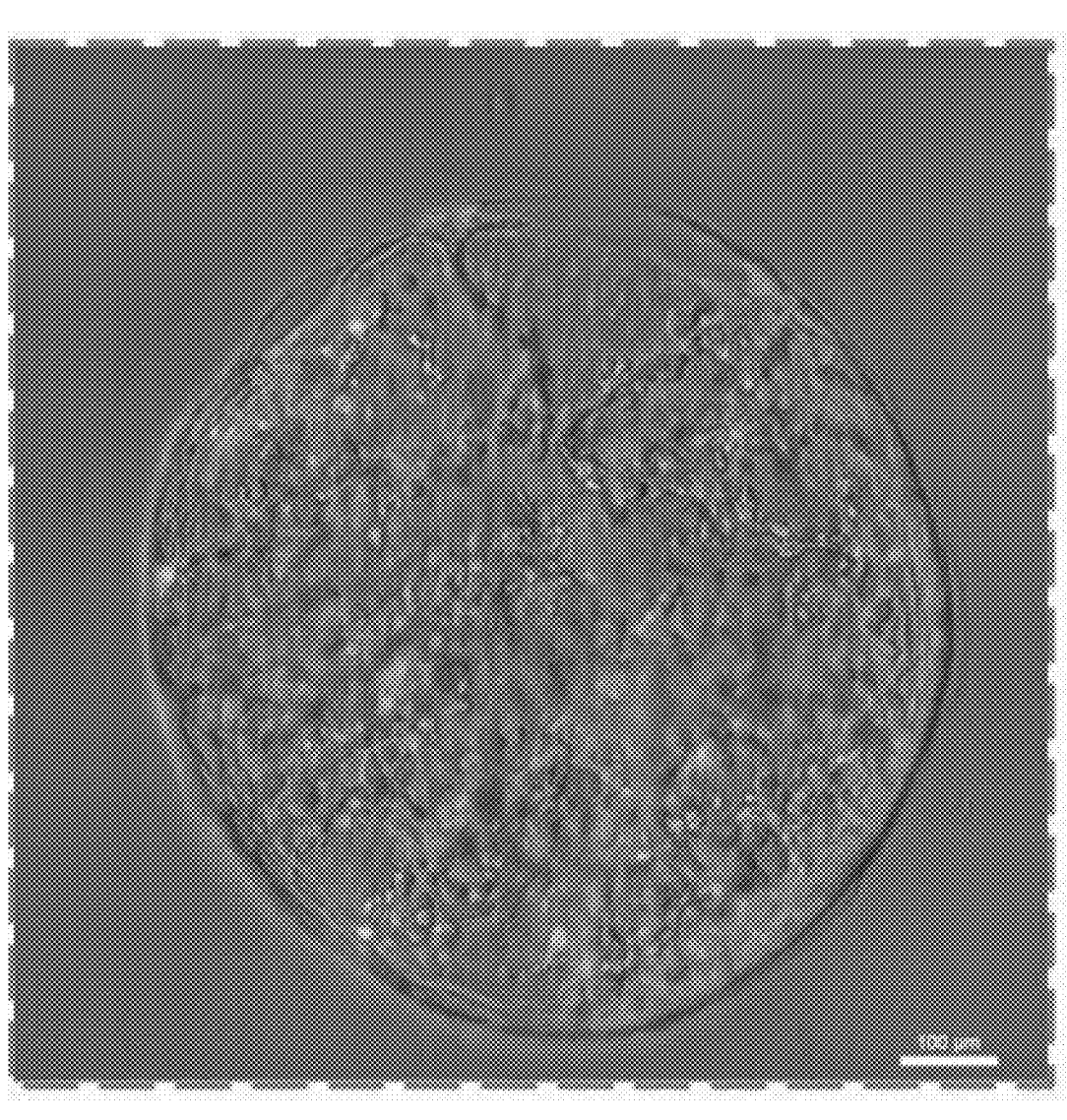
FIG. 21B includes a photograph with a close-up view of one of the hydrogel posts of FIG. 21A 1 day post-printing.

The cells were allowed to grow for 24 hours and re-imaged as shown in FIG. 21B. The image shows cell encapsulation and initial signs of cell extension one-day post-printing.

Figure 22:
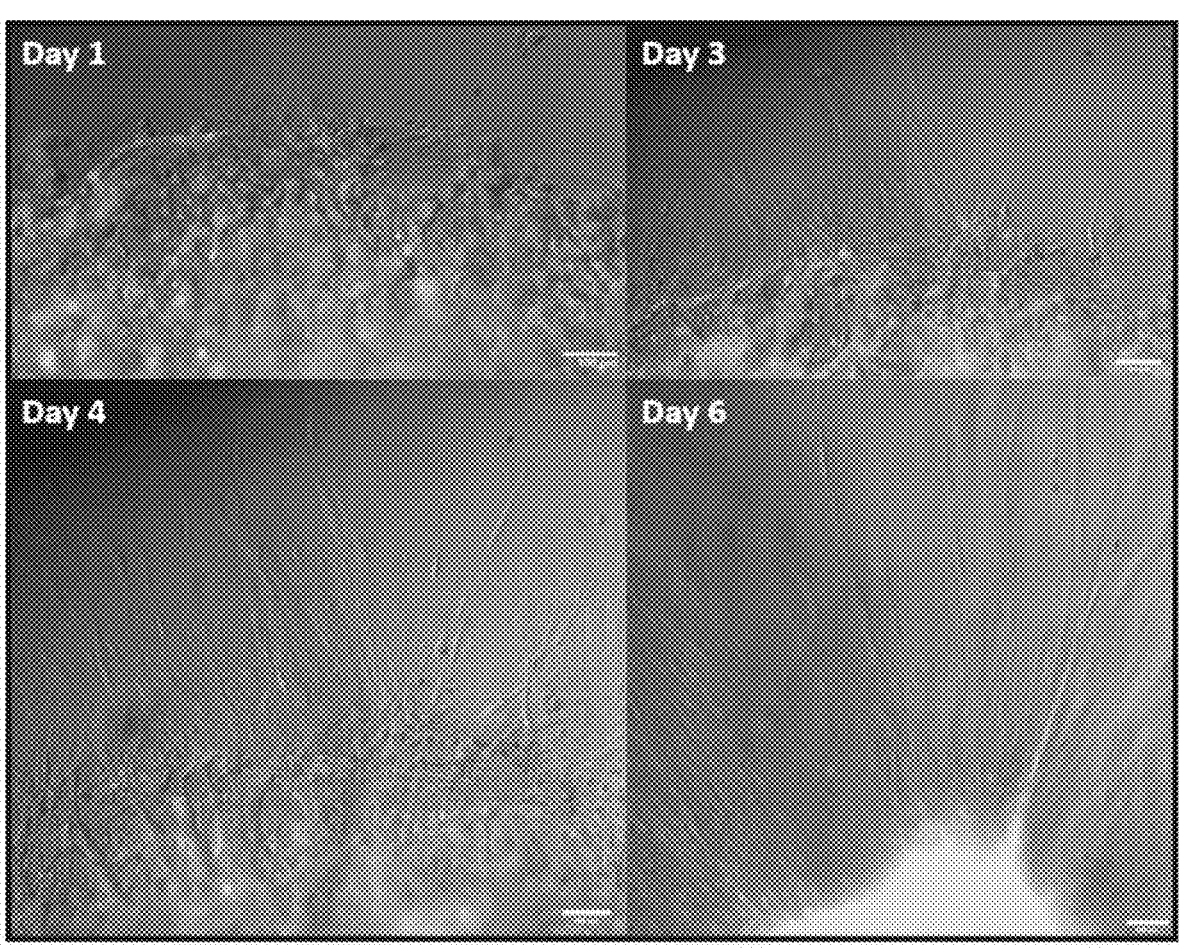
FIG. 22 includes overlayed phase contrast and fluorescent images of hMSCs expressing EGFP in the cytoplasm and H2B-mCherry in the nucleus. Scale bar=100 μm.

Example 3: Cell Migration hMSC cells were photopolymerized in a small droplet of 10 wt % PEG-HD 1.5:1 with 5 mM acryloyl-PEG-CGRGDS hydrogel and then casted within a fibrin gel. Small hMSC extensions into the surrounding fibrin gel were observed after a day after the bioactive hydrogels were casted in fibrin (see FIG. 22). Long hMSC extensions into the fibrin gel were observed after 4 days while even more significant extensions into the surrounding fibrin was observed after 6 days in culture.

Example 4: Encapsulated Cell Viability/Function hMSCs were printed in a single layer, encapsulated in PEG-based gels. The cells were cultured for 2 days and live/dead stained. The cells were found to be over 90% viable and to have invaded the surrounding matrix throughout a week-long culture period, demonstrating that the printing process did not disrupt the ability of the encapsulated cells to probe their microenvironment, migrate, and proliferate.

Figure 24A:
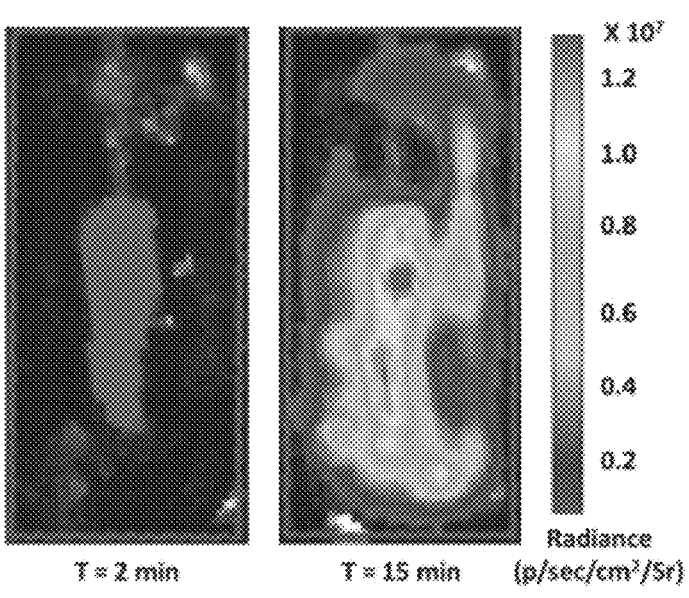
FIG. 24A includes bioluminescence images of a hydrogel with a single channel and embedded HEK293T cells to which luciferin substrate has been perfused at 2 minutes and 15 minutes post-perfusion.
Figure 24B:
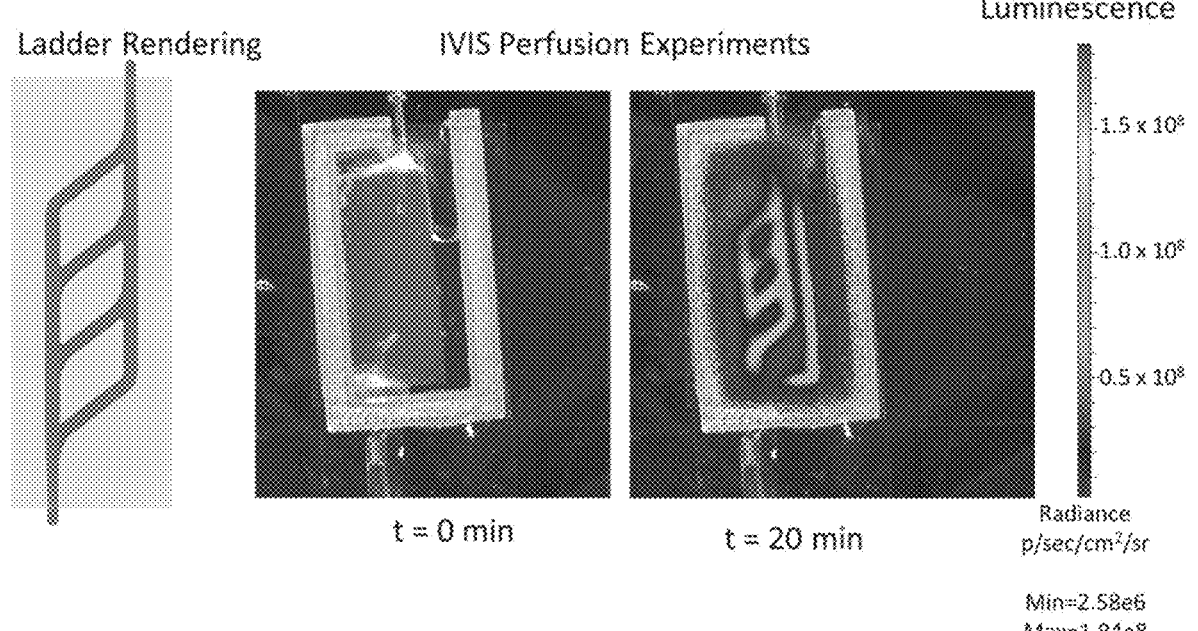
FIG. 24B includes bioluminescence images of a hydrogel with a vascular ladder channel and embedded HEK293T cells to which luciferin substrate has been perfused at 0 minutes and 20 minutes post-perfusion.

Luc2P-expressing HEK293T cells were added to a prepolymerization solution to encapsulate cells into a multilayered 3D hydrogel comprising a single channel traversing the gel horizontally. After 5 days in culture, luciferin substrate was perfused into the channel and bioluminescence images captured at two minutes and fifteen minutes postperfusion (sec FIG. 24A). The images show that cell survival was dependent on the printed network architecture. A similar experiment was performed using a Vascular Ladder architecture with images captured at zero and twenty minutes post-perfusion (see FIG. 24B).

Example 5: Bioprinting of Macroporous Structures

Figure 25A:
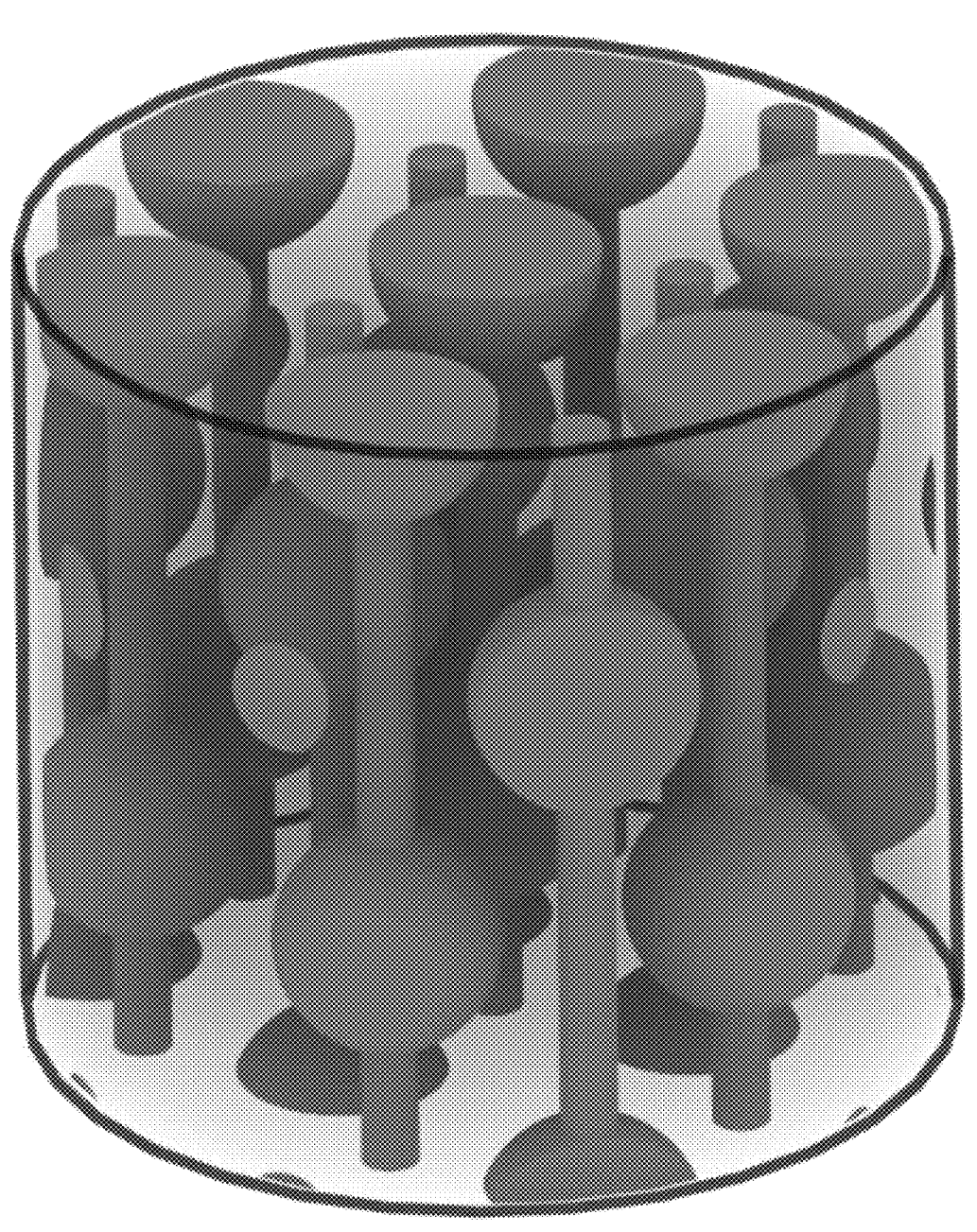
FIG. 25A depicts a cylindrical porous model containing smaller cylinders and spheres.
Figure 25B:
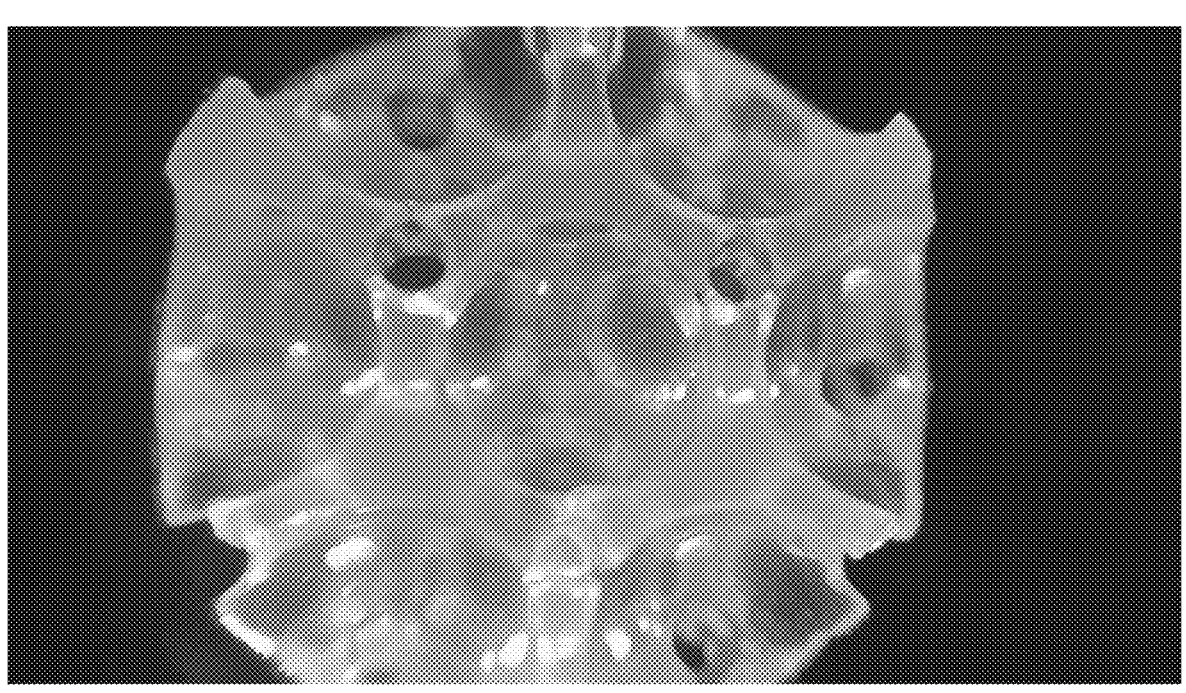
FIG. 25B includes a photograph of a PEG hydrogel based on the cylindrical porous model of FIG. 25A after incubation in a red fluorescent solution.

A 3D cylindrical porous model containing smaller cylinders and spheres is shown in FIG. 25A. The 3D cylindrical porous model was printed as a PEG hydrogel which was incubated in a red fluorescent solution and imaged using a camera as shown in FIG. 25B.

Figure 26A:
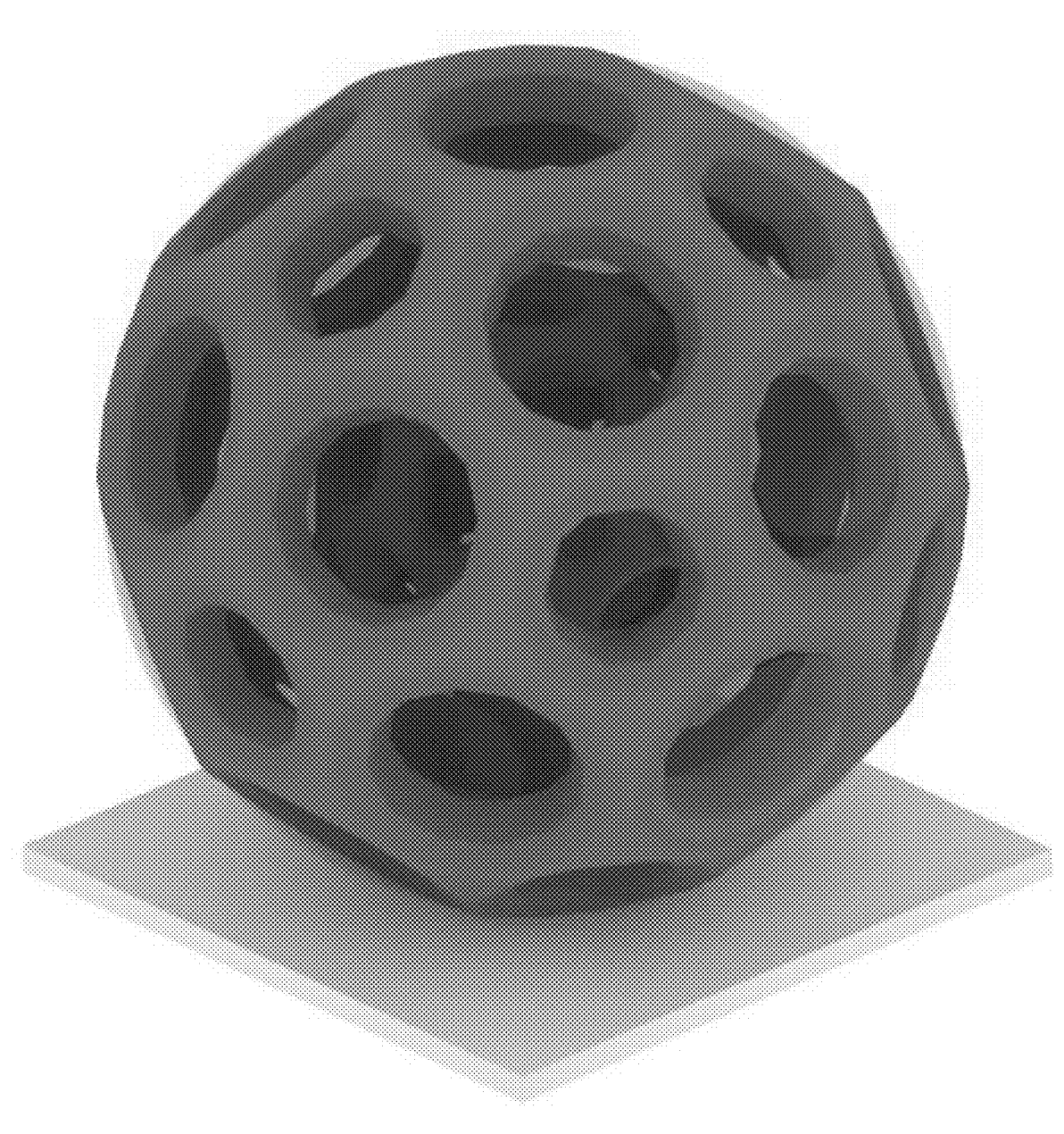
FIG. 26A depicts a meshball model containing a smaller meshball inside.
Figure 26B:
FIG. 26B includes a photograph of a PEG hydrogel based on the meshball model of FIG. 26A after incubation in a green fluorescent solution.

A 3D meshball model containing a smaller meshball inside is shown in FIG. 26A. The 3D meshball model of FIG. 26A was printed as a PEG hydrogel and incubated in a green fluorescent solution and imaged using a camera as shown in FIG. 26B.

These models demonstrate the use of the present approach to produce complex porous architectures. Such architectures can be useful in bone tissue engineering, in which mimicking the spongy architecture of trabecular bone is desirable.

Therefore, the present invention is well adapted to attain the ends and advantages mentioned as well as those that are inherent therein. While numerous changes may be made by those skilled in the art, such changes are encompassed within the spirit of this invention as illustrated, in part, by the appended claims.

Example 6: Oxygenation of Red Blood Cells by Perfusion of Oxygen

Figure 28:
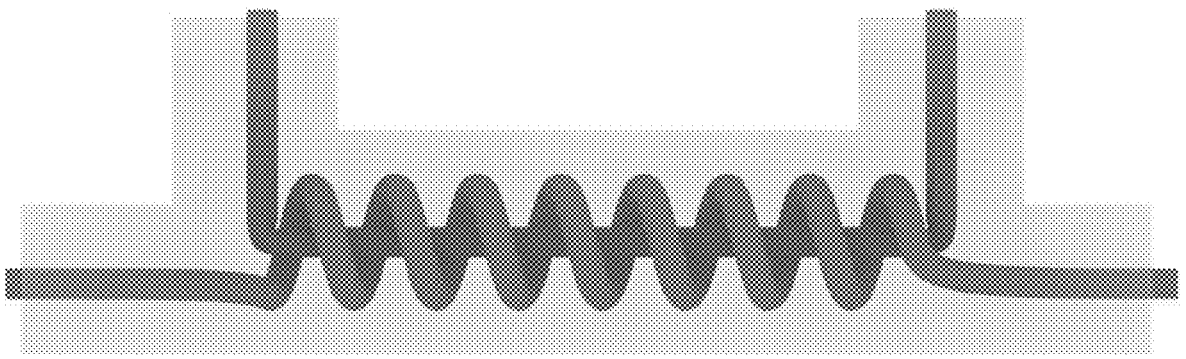
FIG. 28 depicts a hydrogel matrix that includes a U-shaped channel interpenetrated by a spiral channel surrounding the U-shaped channel.

To investigate the potential for oxygenating red blood cells in a hydrogel containing interpenetrating networks, a hydrogel matrix was produced that included a U-shaped channel interpenetrated by a spiral channel surrounding the U-shaped channel (see FIG. 28). The hydrogel matrix was prepared from a prepolymerization solution containing 20 wt % 6 kDa PEGDA, 34 mM LAP and 1.59 mM tartrazine. The channels were 0.8 mm in diameter with 0.6 mm spacing between the walls of the channels. The hydrogel matrix was printed at a layer thickness of 100 μm.

Figure 29A:
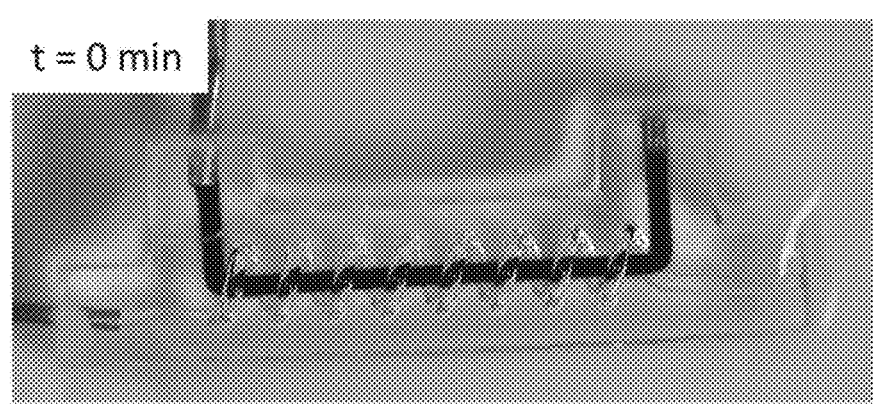
FIG. 29A includes a photographs of a PEG hydrogel at 0, 15 and 30 minutes where deoxygenated blood was placed in the U-shaped channel of a hydrogel of the design of FIG. 28 and nitrogen was perfused through the spiral channel for 15 minutes followed by perfusion of oxygen.
Figure 29A:
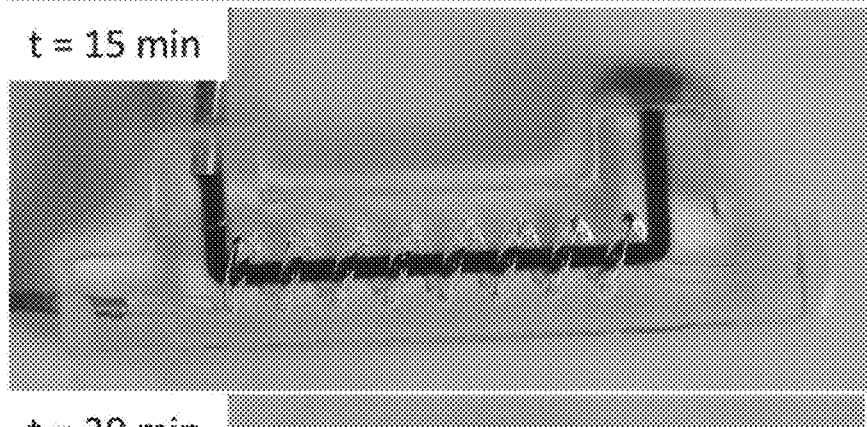
Figure 29A:
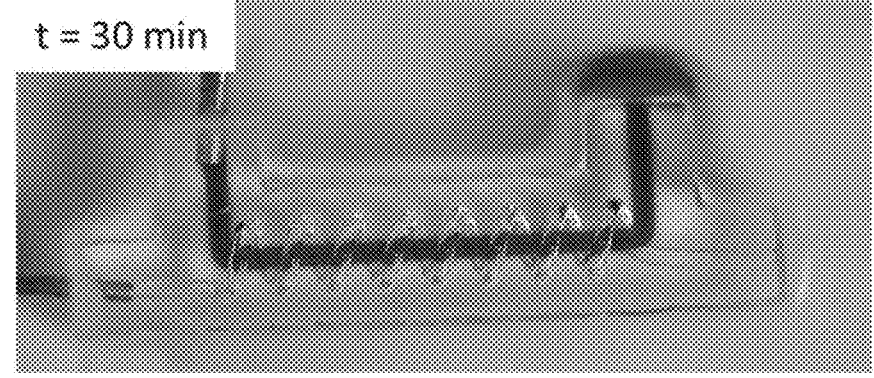

Deoxygenated human packed red blood cells (RBCs) were obtained by gently bubbling blood under nitrogen for 30 minutes. The blood became dark red and was analyzed using a blood gas analyzer (Siemens RAPIDPoint 500) which measured a pO$_2$ of about 21 mmHg in the deoxygenated blood. A portion of the deoxygenated blood was gently bubbled for 30 minutes to confirm its oxygenation potential. The blood became bright red and oxygenation was confirmed using the blood gas analyzer which measured a pO$_2$ over 100 mmHg. The deoxygenated blood was perfused into the U-shaped channel of the hydrogel matrix until the blood was about 2 mm away from the outlet of the U-shaped channel. Humidified nitrogen was perfused through the spiral channel at 1 psi for 15 minutes followed by perfusing humidified oxygen at 1 psi through the spiral channel for an additional 15 minutes. Images were captured at 0, 15 and 30 minutes from the start of perfusing nitrogen into the spiral channel (see FIG. 29A). As can be observed, the blood was dark red at the start of the experiment, indicating deoxygenation of the blood which was confirmed by the blood gas analyzer results. After 15 minutes of perfusing nitrogen, most of the blood was still dark red indicating that is was still deoxygenated. After 15 minutes of perfusing oxygen, most of the blood had become bright red, indicating oxygenation of the blood.

Figure 29B:
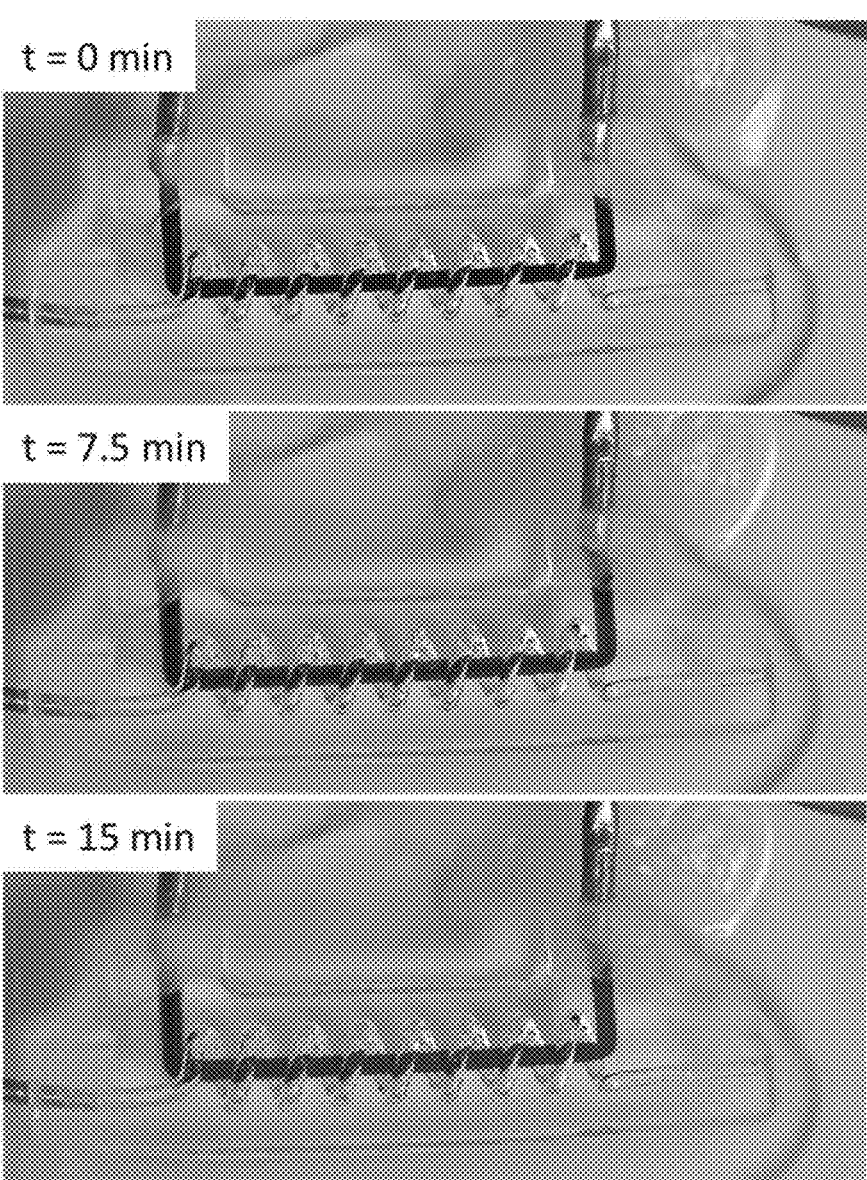
FIG. 29B includes a photographs of a PEG hydrogel at 0, 7.5 and 15 minutes where deoxygenated blood was placed in the U-shaped channel of a hydrogel of the design of FIG. 28 and oxygen was perfused through the spiral channel.

In a separate experiment, deoxygenated blood was prepared similarly by bubbling under nitrogen for 30 minutes. The deoxygenated blood was then perfused into the U-shaped channel until it was about 2 mm away from the outlet. Humidified oxygen was perfused through the spiral channel at 1 psi for 15 minutes. Images were captured at 0, 7.5 and 15 minutes from the start of perfusing oxygen into the spiral channel (see FIG. 29B). As can be observed, after 15 minutes of oxygen perfusion, the blood in the U-shaped channel became bright red indicating oxygenation of the red blood cells.

These results demonstrate exchange of oxygen from the spiral channel to the U-shaped channel and oxygenation of the red blood cells using a hydrogel matrix with interpenetrating channels.

Example 7: Oxygenation of Red Blood Cells Across a Branching Airway Containing Functional Epithelium A hydrogel matrix comprising PEGDA with RGDS can be produced and allowed to reach swelling equilibrium. The airway channel can then be epithelialized with HBEC-3kt cells. Then, using a syringe pump, sterile filtered air can be perfused through the epithelialized airway channel while red blood cells are perfused through the vascular channel at specific rates. Oxygen can then diffuse from the airway channel to the vascular channel, oxygenating the red blood cells.

What is claimed is:
1. A prepolymerization solution, comprising:
poly(ethylene glycol) having a molecular weight of greater than 2,000 Daltons and comprising at least two acrylate groups per molecule of poly(ethylene glycol);
a photo-initiator; and
a protein with a peak light absorption overlapping that of the photo-initiator.
2. The prepolymerization solution of claim 1, wherein the prepolymerization solution excludes a light-absorbing additive material.
3. The prepolymerization solution of claim 1, wherein the prepolymerization solution further comprises a biocompatible, light-absorbing additive material, wherein the biocompatible, light-absorbing additive material has an additional capability to cause printing, by controlling light penetration, a structure with horizontal and vertical channels.
4. The prepolymerization solution of claim 1, further comprising a cell, wherein the cell is transfected or transduced with the protein.

5. The prepolymerization solution of claim 1, wherein the protein is a cyan fluorescent protein (CFP) or a green fluorescent protein (GFP).

6. The prepolymerization solution of claim 1, further comprising a cryoprotectant.

7. The prepolymerization solution of claim 4, further comprising a medium configured to provide nutrition and/or buoyancy for the cell.

\* \* \* \* \*